United States Patent
High

(10) Patent No.: US 10,722,357 B2
(45) Date of Patent: Jul. 28, 2020

(54) FLUSHABLE LOADING BASE

(71) Applicant: St. Jude Medical, Cardiology Division, Inc., St. Paul, MN (US)

(72) Inventor: Keith High, White Bear Lake, MN (US)

(73) Assignee: St. Jude Medical, Cardiology Division, Inc., St. Paul, MN (US)

( * ) Notice: Subject to any disclaimer, the term of this patent is extended or adjusted under 35 U.S.C. 154(b) by 190 days.

(21) Appl. No.: 16/037,187

(22) Filed: Jul. 17, 2018

(65) Prior Publication Data

US 2019/0021856 A1   Jan. 24, 2019

Related U.S. Application Data

(60) Provisional application No. 62/533,755, filed on Jul. 18, 2017.

(51) Int. Cl.
*B25B 13/00* (2006.01)
*H02G 1/00* (2006.01)
(Continued)

(52) U.S. Cl.
CPC .......... *A61F 2/2427* (2013.01); *A61F 2/2418* (2013.01); *A61M 5/36* (2013.01);
(Continued)

(58) Field of Classification Search
CPC .......... B23Q 3/00; B23Q 3/154; B23Q 11/00; B25B 11/00; B25B 11/02
See application file for complete search history.

(56) References Cited

U.S. PATENT DOCUMENTS 3,657,744 A    4/1972 Ersek
4,423,730 A    1/1984 Gabbay
(Continued)

FOREIGN PATENT DOCUMENTS

EP    1129744 A1    9/2001
EP    1157673 A2    11/2001
(Continued)

OTHER PUBLICATIONS

International Search Report including Written Opinion for PCT/US2018/042361 dated Sep. 24, 2018.
(Continued)

*Primary Examiner* — Lee D Wilson
(74) *Attorney, Agent, or Firm* — Lerner, David, Littenberg, Krumholz & Mentlik, LLP

(57) ABSTRACT

An assembly for loading a self-expanding prosthetic heart valve into a delivery device includes a support member including a body and a backing plate. The body has a longitudinal axis, a base end, a second end, and a recess extending along the longitudinal axis from the second end toward the base end. The recess has a bottom member defining a seating surface adapted to support the prosthetic heart valve. The backing plate is fixed to the body so as to define a void space between the backing plate and the body. The backing plate includes an inlet port and the recess includes a plurality of outlet ports. The inlet and outlet ports are in fluid communication with the void space. When the heart valve is received on the seating surface, each outlet port is rotationally aligned with a corresponding pocket formed between first and second cuffs of the heart valve.

20 Claims, 18 Drawing Sheets

(51) Int. Cl.
*A61F 2/24* (2006.01)
*A61M 5/36* (2006.01)
*A61F 2/00* (2006.01)
*A61F 2/95* (2013.01)

(52) U.S. Cl.
CPC .......... *A61F 2/0095* (2013.01); *A61F 2/2436* (2013.01); *A61F 2002/9505* (2013.01); *A61F 2002/9522* (2013.01)

(56) References Cited

U.S. PATENT DOCUMENTS

| | | |
|---|---|---|
| 5,843,167 A | 12/1998 | Dwyer et al. |
| 5,924,424 A | 7/1999 | Stevens et al. |
| 5,968,068 A | 10/1999 | Dehdashtian et al. |
| 6,068,635 A | 5/2000 | Gianotti |
| 6,077,297 A | 6/2000 | Robinson et al. |
| 6,132,458 A | 10/2000 | Staehle et al. |
| 6,306,141 B1 | 10/2001 | Jervis |
| 6,471,718 B1 | 10/2002 | Staehle et al. |
| 6,623,518 B2 | 9/2003 | Thompson et al. |
| 6,814,746 B2 | 11/2004 | Thompson et al. |
| 6,830,584 B1 | 12/2004 | Seguin |
| 6,935,389 B1 | 8/2005 | Rinaldi |
| 7,014,074 B1 | 3/2006 | Rinaldi |
| 7,018,406 B2 | 3/2006 | Seguin et al. |
| 7,096,554 B2 | 8/2006 | Austin et al. |
| 7,311,730 B2 | 12/2007 | Gabbay |
| 7,510,572 B2 | 3/2009 | Gabbay |
| 7,682,390 B2 | 3/2010 | Seguin |
| 7,803,185 B2 | 9/2010 | Gabbay |
| 8,561,967 B2 | 10/2013 | Hendriksen et al. |
| 8,562,663 B2 | 10/2013 | Mearns et al. |
| 8,585,019 B2 | 11/2013 | Melsheimer et al. |
| 8,931,159 B2 | 1/2015 | Hillukka |
| 8,973,234 B2 | 3/2015 | Johnson et al. |
| 9,021,674 B2 | 5/2015 | Hillukka et al. |
| 9,192,469 B2 | 11/2015 | Mearns et al. |
| 9,414,914 B2 | 8/2016 | Duffy et al. |
| 9,414,917 B2 | 8/2016 | Young et al. |
| 9,492,274 B2 | 11/2016 | Johnson et al. |
| 9,675,456 B2 | 6/2017 | Quill et al. |
| 10,575,949 B2 * | 3/2020 | Morin .................. A61F 2/2427 |
| 2002/0096468 A1 | 7/2002 | Zuk |
| 2003/0050694 A1 | 3/2003 | Yang et al. |
| 2003/0070682 A1 | 4/2003 | Wilson et al. |
| 2004/0210304 A1 | 10/2004 | Seguin et al. |
| 2005/0137695 A1 | 6/2005 | Salahieh et al. |
| 2005/0137697 A1 | 6/2005 | Salahieh et al. |
| 2005/0194578 A1 | 9/2005 | Morris |
| 2006/0074484 A1 | 4/2006 | Huber |
| 2006/0106415 A1 | 5/2006 | Gabbay |
| 2006/0135973 A1 | 6/2006 | Hawkins et al. |
| 2006/0142848 A1 | 6/2006 | Gabbay |
| 2006/0167468 A1 | 7/2006 | Gabbay |
| 2006/0259120 A1 | 11/2006 | Vongphakdy et al. |
| 2007/0010876 A1 | 1/2007 | Salahieh et al. |
| 2007/0027534 A1 | 2/2007 | Bergheim et al. |
| 2007/0043435 A1 | 2/2007 | Seguin et al. |
| 2007/0055358 A1 | 3/2007 | Krolik et al. |
| 2007/0073391 A1 | 3/2007 | Bourang et al. |
| 2007/0088431 A1 | 4/2007 | Bourang et al. |
| 2007/0112422 A1 | 5/2007 | Dehdashtian |
| 2007/0162100 A1 | 7/2007 | Gabbay |
| 2007/0168013 A1 | 7/2007 | Douglas |
| 2007/0203575 A1 | 8/2007 | Forster et al. |
| 2007/0239271 A1 | 10/2007 | Nguyen |
| 2007/0244552 A1 | 10/2007 | Salahieh et al. |
| 2007/0270931 A1 | 11/2007 | Leanna et al. |
| 2007/0270932 A1 | 11/2007 | Headley et al. |
| 2008/0071369 A1 | 3/2008 | Tuval et al. |
| 2008/0147182 A1 | 6/2008 | Righini et al. |
| 2008/0221703 A1 | 9/2008 | Que et al. |
| 2009/0054975 A1 | 2/2009 | del Nido et al. |
| 2009/0093876 A1 | 4/2009 | Nitzan et al. |
| 2009/0143857 A1 | 6/2009 | Melsheimer et al. |
| 2010/0004740 A1 | 1/2010 | Seguin et al. |
| 2010/0051886 A1 | 3/2010 | Cooke et al. |
| 2010/0286768 A1 | 11/2010 | Alkhatib |
| 2010/0298931 A1 | 11/2010 | Quadri et al. |
| 2011/0224678 A1 | 9/2011 | Gabbay |
| 2011/0257734 A1 | 10/2011 | Chalekian |
| 2011/0282287 A1 | 11/2011 | Chalekian |
| 2012/0078352 A1 | 3/2012 | Wang et al. |
| 2012/0083875 A1 | 4/2012 | Johnson et al. |
| 2012/0330408 A1 | 12/2012 | Hillukka et al. |
| 2013/0190859 A1 | 7/2013 | Hillukka |
| 2014/0331475 A1 | 11/2014 | Duffy et al. |
| 2015/0101171 A1 | 4/2015 | Johnson et al. |
| 2016/0128819 A1 | 5/2016 | Giordano et al. |
| 2016/0278955 A1 | 9/2016 | Liu et al. |
| 2017/0035570 A1 | 2/2017 | Johnson et al. |
| 2019/0021856 A1 * | 1/2019 | High .................... A61F 2/2427 |
| 2019/0117394 A1 * | 4/2019 | Morin .................. A61F 2/2427 |

FOREIGN PATENT DOCUMENTS

| | | |
|---|---|---|
| JP | 2000093523 A | 4/2000 |
| JP | 2009533139 A | 9/2009 |
| WO | 07071436 A2 | 6/2007 |
| WO | 2007081940 A2 | 7/2007 |
| WO | 2007120543 A1 | 10/2007 |
| WO | 08070797 A2 | 6/2008 |
| WO | 2009091509 A1 | 7/2009 |
| WO | 2010014834 A1 | 2/2010 |
| WO | 10051025 A1 | 5/2010 |
| WO | 10087975 A1 | 8/2010 |
| WO | 2010096176 A1 | 8/2010 |
| WO | 2011100745 A2 | 8/2011 |
| WO | 2012023979 A2 | 2/2012 |
| WO | 2012036742 A2 | 3/2012 |
| WO | 2012036744 A2 | 3/2012 |
| WO | 2012057983 A1 | 5/2012 |
| WO | 2012106491 A1 | 8/2012 |

OTHER PUBLICATIONS

Ruiz, Carlos, Overview of PRE-CE Mark Transcatheter Aortic Valve Technologies, Euro PCR, dated May 25, 2010.
International Search Report and Written Opinion for Application No. PCT/US2012/023576 dated Jul. 6, 2012.
International Search Report for Application No. PCT/US2012/048307 dated Feb. 28, 2013.
International Search Report for Application No. PCT/US2012/048298 dated Nov. 7, 2012.
Quaden et al., "Percutaneous aortic valve replacement: resection before implantation", pp. 836-840, European J. of Cardio-thoracic Surgery, 27 (2005).
International Search Report for Application No. PCT/US2011/001598 dated Jul. 6, 2012.
Medtronic, "CoreValve Percutaneous Aortic Valve Implantation System", Brochure, 8 pages, Copyright 2009.
Medtronic CoreValve™ System, Instructions for Use, 61 pages (2014).
Medtronic, "Loading Heart Valve Catheter", Medical & Scientific Video Production, 59 video screen shots, Copyright 2006.

* cited by examiner

US 10,722,357 B2

FLUSHABLE LOADING BASE

CROSS-REFERENCE TO RELATED APPLICATIONS

This application claims the benefit of the filing date of U.S. Provisional Patent Application No. 62/533,755 filed Jul. 18, 2017, the disclosure of which is hereby incorporated by reference herein.

BACKGROUND OF THE DISCLOSURE

The present disclosure relates to prosthetic heart valve implantation and, more particularly, to assemblies and methods for loading a self-expanding collapsible heart valve into a delivery device.

Prosthetic heart valves may be formed from biological materials such as harvested bovine valves or pericardial tissue. Such prosthetic valves are typically fitted within a stent, which may be inserted into the heart at the annulus of the compromised native valve to replace the functioning of the native valve. To perform such insertion procedure using a minimally invasive technique, it is typically necessary to compress the stent to a reduced diameter for loading into the delivery device.

In the case of prosthetic valves formed from biological materials, the stented valve is preferably preserved in the open condition for storage as compression of the valve material for extended periods may compromise the integrity of the biological valve. It may therefore be necessary to crimp the valve, or reduce its diameter for loading into the delivery device, in the operating arena.

Present crimping devices and methods for collapsing a stented valve, including direct radial assemblies, have proven to be unsatisfactory as they include bulky assemblies, are difficult to master, are time consuming to use, impart undue stress on the stented valve, and/or exhibit other undesirable qualities. Moreover, it is sometimes difficult to securely engage the stent with a retaining element of the delivery device. Further, prosthetic heart valves that incorporate two separate cuff layers may present particular difficulties in loading the valve into the delivery device, which are not encountered with prosthetic heart valves that incorporate a single cuff layer. It would therefore be beneficial to be able to collapse a stented bioprosthetic heart valve using apparatus and techniques that overcome the deficiencies of conventional devices. In addition, such devices and methods could be useful in loading the collapsed stented valve into a minimally invasive delivery device.

BRIEF SUMMARY

According to one aspect of the disclosure, an assembly for loading a self-expanding prosthetic heart valve into a delivery device includes a support member including a generally hollow body and a backing plate. The body has a longitudinal axis, a base end, a second end, and a recess extending along the longitudinal axis from the second end toward the base end. The recess has a bottom member defining a seating surface adapted to support the prosthetic heart valve, the backing plate being fixed to the body so as to define a void space between the backing plate and the body. The backing plate includes an inlet port and the recess includes a plurality of outlet ports, the inlet port and the outlet ports being in fluid communication with the void space.

DETAILED DESCRIPTION

Figure 1:
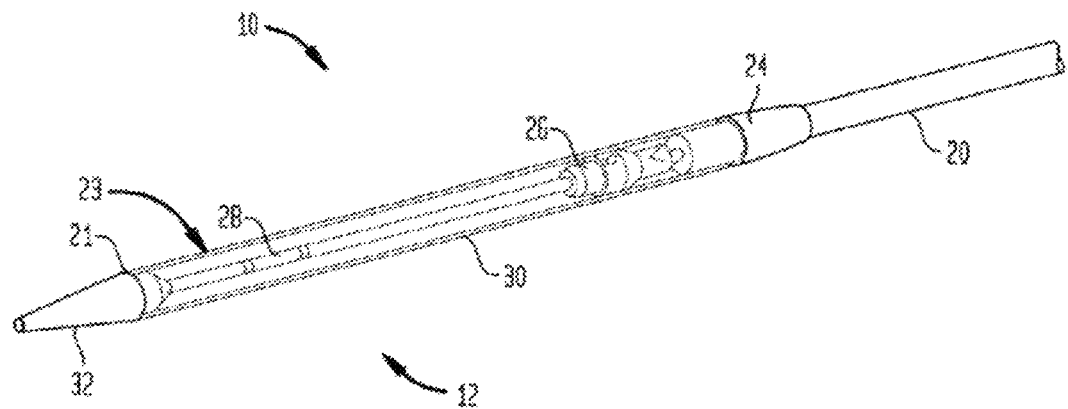
FIG. 1 is a perspective view of a distal portion of a delivery device.

Embodiments of the presently disclosed loading assemblies are described herein in detail with reference to the drawing figures, wherein like reference numerals identify similar or identical elements. In the drawings and in the description which follows, the term "proximal" refers to the end of the loading assembly, or portion thereof, which is closest to the operator when in use as intended, while the term "distal" refers to the end of the loading assembly, or portion thereof, which is farthest from the operator when in use as intended.

Figure 2:
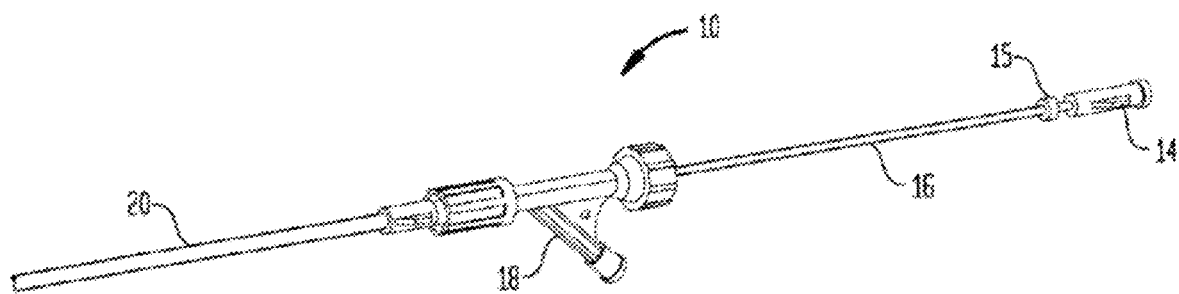
FIG. 2 is a perspective view of a proximal portion of the delivery device of FIG. 1.

The present disclosure relates to assemblies and methods for loading a self-expanding stent or a collapsible prosthetic heart valve into a minimally invasive delivery device. An exemplary minimally invasive delivery device 10 is illustrated in FIGS. 1 and 2.

An exemplary delivery device 10 for transfemoral delivery of a collapsible prosthetic heart valve (or other types of self-expanding collapsible stents) has a catheter assembly 12 for delivering the heart valve to and deploying the heart valve at a target location. Catheter assembly 12 includes a compartment 23 defined between an atraumatic tip 32 of delivery device 10 and a retaining element 26. A support shaft 28 is connected between tip 32 and retaining element 26 and defines the length of compartment 23. A distal sheath 30 is slidably arranged relative to compartment 23 so that, in a distalmost or closed position in which the distal end 21 of the sheath abuts atraumatic tip 32, the sheath covers the prosthetic heart valve and retains it in a collapsed condition for delivery to the target site, and in a proximal or open position in which the distal end of the sheath is spaced from the atraumatic tip, the sheath uncovers the prosthetic heart valve for deployment at the target site.

An inner tube 16 having a lumen therethrough extends from a hub 14 at or near its proximal end to a distal end which may be connected to retaining element 26. Optionally, the distal end of inner tube 16 may extend through retaining element 26 and support shaft 28 for connection to atraumatic tip 32. In either arrangement, the distal end of inner tube 16 is operably connected to compartment 23 so as to define a fixed distance between hub 14 and the compartment. The lumen through inner tube 16 is sized to slidingly receive a guidewire (not shown) for use in guiding the delivery device to the target site. At its proximal end, inner tube 16 may be provided with a hemostasis valve (not shown) for preventing, or at least hindering, blood flow out from the inner tube.

Hub 14, or a portion of inner tube 16 adjacent the hub, is adapted for connection to another system or mechanism, such as an operating handle (not shown) for translating distal sheath 30. Mechanisms for translating distal sheath 30 between its proximal and distal positions are described in International Patent Application Publication No. WO/2009/091509, the disclosure of which is hereby incorporated by reference herein. A retaining ring 15 may be mounted on inner tube 16 near hub 14.

Catheter assembly 12 further includes an outer shaft 20 which is connected at its distal end through tapered transition member 24 to the proximal end of distal sheath 30, and at its proximal end to the operating handle (not shown). A Y-connector 18 may also be connected at the proximal end of outer shaft 20, and may include a hemostasis valve for hindering blood flow out from between inner tube 16 and outer shaft 20. Y-connector 18 may also be coupled to a fluid source for flushing outer shaft 20, injecting contrast media during a prosthetic valve implantation procedure, and the like. Similar delivery devices that may be suitable for use with the prosthetic heart valves and loading assemblies described herein are also described in U.S. Provisional Patent Application No. 62/506,251, filed May 15, 2017 and titled "TRANSCATHETER DELIVERY SYSTEM WITH WHEEL ACTUATION," the disclosure of which is hereby incorporated by reference herein.

Figure 3:
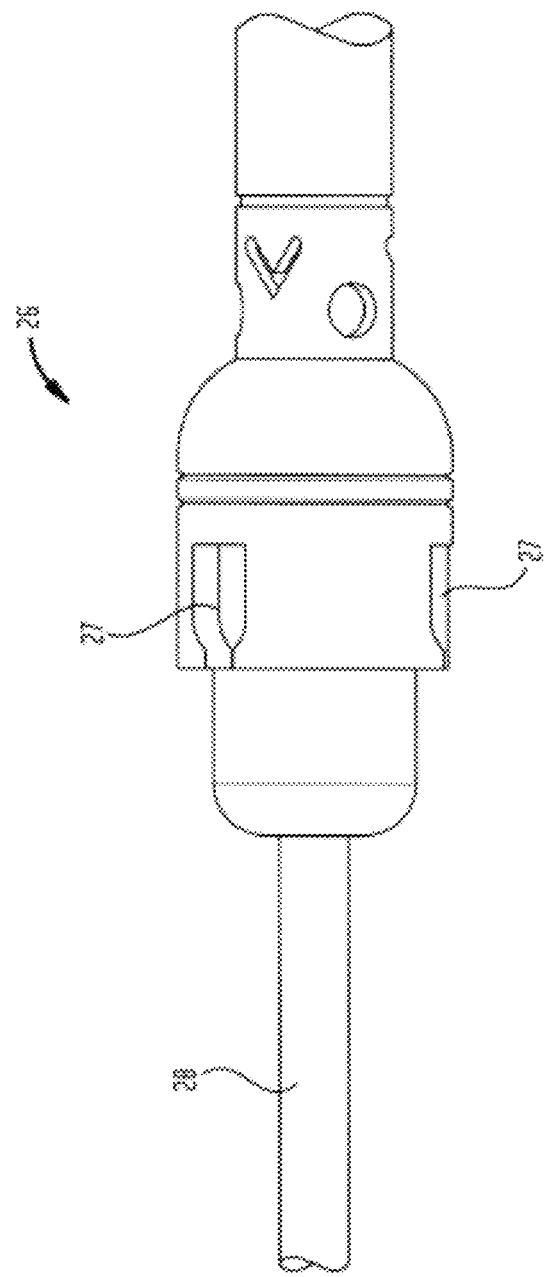
FIG. 3 is an enlarged side view of a retaining element of the delivery device shown in FIGS. 1 and 2.

As shown in FIG. 3, retaining element 26 may include a plurality of recesses 27 located around its periphery. Recesses 27 are spaced apart from one another and each is sized and shaped to receive a tab or retainer on one end of the prosthetic heart valve to maintain the prosthetic heart valve in assembled relationship with delivery device 10, to minimize longitudinal movement of the prosthetic heart valve relative to the delivery device during unsheathing and resheathing procedures, to help prevent rotation of the prosthetic heart valve relative to the delivery device as the delivery device is advanced to the target site and during deployment, and to maintain the alignment of the stent cells and prevent them from becoming tangled.

Figure 4:
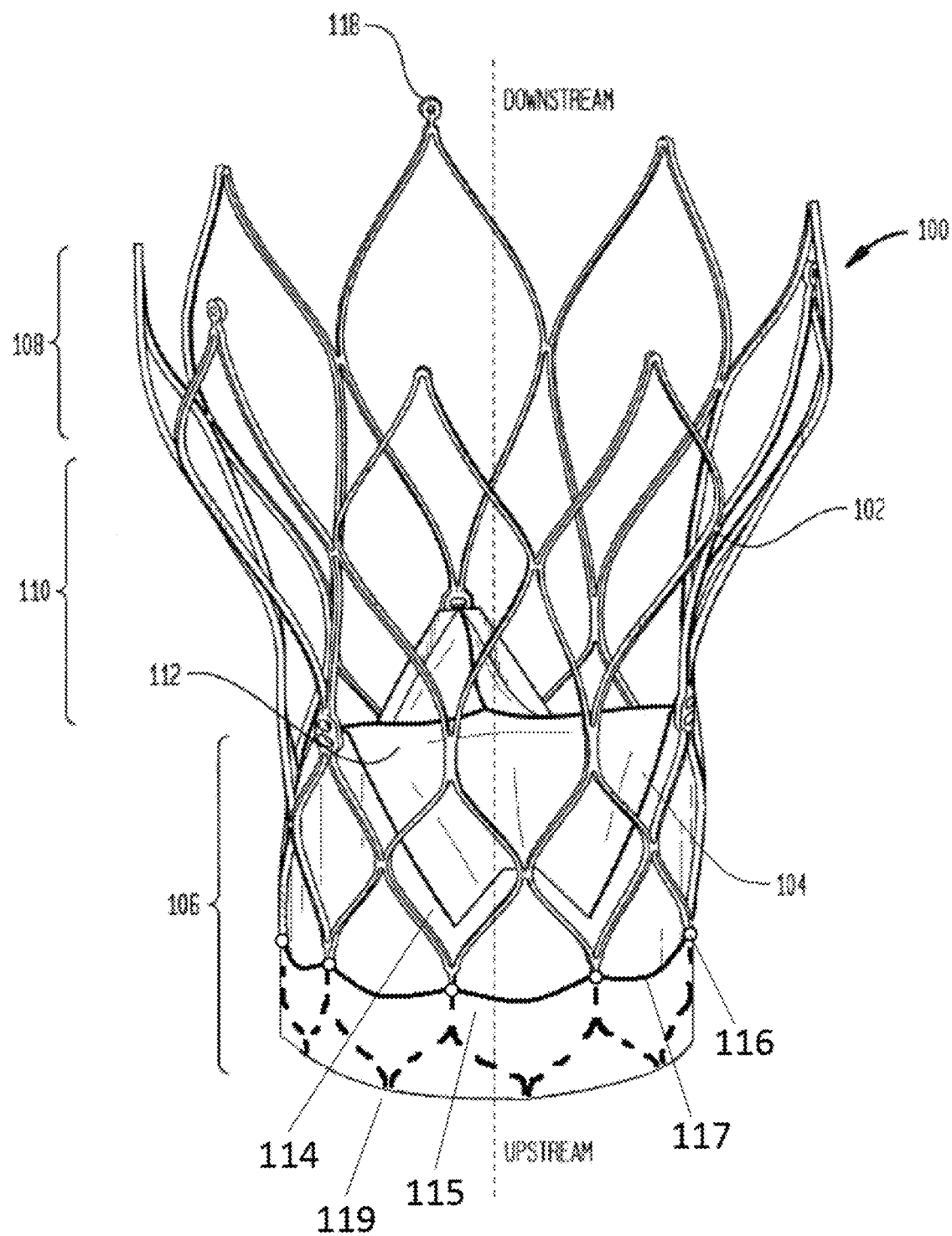
FIG. 4 is a perspective view of a self-expanding prosthetic heart valve.

FIG. 4 shows a prosthetic valve 100 designed to replace a native aortic valve. Valve 100 has a collapsed condition and an expanded condition and may be formed from a collapsible framework or stent 102, with a valve assembly 104 connected to the stent. Stent 102 may be formed from any suitable biocompatible material, such as nitinol or any other suitable elastic or shape memory material, and may include an annulus section 106, an aortic section 108, and a transition or sinus section 110 located between the annulus section and the aortic section. Aortic section 108 may have a larger transverse cross-section than annulus section 106. Valve assembly 104 includes a plurality of leaflets 112, a first cuff 114 attached to the stent 102, and a second cuff 115 attached to the stent and/or the first cuff and positioned radially outward of the stent. Leaflets 112, first cuff 114, and second cuff 115 may be formed from a biocompatible polymer, from natural tissue such as bovine or porcine pericardial tissue, or from other appropriate biocompatible materials. Valve assembly 104 is preferably connected to stent 102 and/or to first cuff 114 generally within annulus section 106. Valve 100 may include a plurality of tabs or retainers 118 at spaced positions around one or both ends of stent 102 for engagement with the recesses 27 in the retaining element 26 of delivery device 10 as described above. Retainers 118 may also be utilized to collapse valve 100 for loading into delivery device 10, as will be discussed below.

Second cuff 115 may extend around the outer circumference of the upstream or inflow end of stent 102. A bottom or inflow edge of second cuff 115 may be coupled to first cuff 114 around the circumference of the inflow edge of stent 102. The inflow edge of second cuff 115 may also be coupled to selected struts of stent 102. In other words, the inflow edges of first cuff 114 and second cuff 115 may both extend to the inflow edge of stent 102 and may couple together so that fluid between the first and second cuffs is hindered or prevented from passing through the coupled inflow edges of the cuffs. The struts of stent 102 positioned between second cuff 115 and first cuff 114 are illustrated in FIG. 4 as dashed lines. These struts may join one another at connection points at the inflow edge of stent 102 and may be referred to as "horseshoes" due to their shape. An outflow or downstream end of second cuff 115 may be coupled to selected struts of stent 102 and/or to selected positions on first cuff 114 at spaced locations around the circumference of the outflow edge of the second cuff. These points of attachment 116 are illustrated in FIG. 4 as open circles and may be made by sutures, adhesives, or any other suitable fastening mechanism. This configuration results in free portions 117 of the outflow edge of second cuff 115 being able to move radially away from first cuff 114 between attachment points 116. After implantation, for example at the native aortic valve, if blood flows in a retrograde direction around the ablumenal surface of stent 102, the blood may flow into the space between second cuff 115 and first cuff 114 between adjacent points of attachment 116, trapping the blood in the pocket(s) formed by the first and second cuff, and restricting the blood from passing back into the left ventricle. If such retrograde blood flow occurs, second cuff 115 may billow outwardly to help seal any gaps between the native heart valve annulus and prosthetic heart valve 100, helping to mitigate the paravalvular leakage of blood.

Valve 100 is preferably stored in its expanded or open condition as the valve assembly 104 may be compromised by storage in a collapsed condition for extended periods of time. As such, it may become necessary to crimp valve 100 into a collapsed condition of reduced cross-section for loading into delivery device 10 at the latest possible time prior to the implantation procedure. In order to effectively limit the time period valve 100 is collapsed, the crimping process is preferably conducted in the operating arena by the surgeon, interventional cardiologist or surgical assistant using a specialized assembly.

Figure 5:
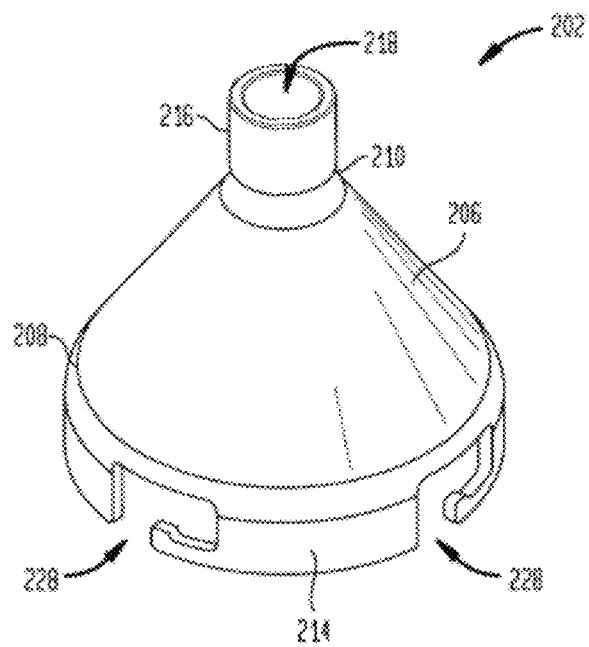
FIG. 5 is a top perspective view of a compression member in accordance with an embodiment of the present disclosure.

FIGS. 5-6 illustrate components of a loading assembly 200 according to one embodiment of the present disclosure, the loading assembly generally including a compression member 202 and a support member 204 adapted to be coupled to one another. Compression member 202 includes a funnel 206 having a substantially frustoconical shape with a large diameter at a first end 208 and a smaller diameter at a second end 210. The diameter of funnel 206 may decrease uniformly from first end 208 to second end 210 to compress the valve 100 as it is advanced through compression member 202. Compression member 202 is preferably made of a substantially rigid material, and may be wholly or partly made of a transparent plastic, such as polycarbonate or acrylic, to allow viewing of valve 100 during loading.

Compression member 202 may further include an annular rim 214 extending from the first end 208 of funnel 206 for joining the compression member to support member 204 as described below. Rim 214 may include a plurality of slots 228 disposed around its outer periphery. While the drawings show slots 228 that are substantially P-shaped, the slots may have any other shape suitable for securely holding compression member 202 to support member 204. Rim 214 may include four such slots 228, or more or less than four. Regardless of the number of slots 228, adjacent slots are preferably spaced equidistantly from each other.

Compression member 202 also may include a tubular extension 216 projecting from the second end 210 of funnel 206. Tubular extension 216 has an opening 218 therethrough in communication with the interior of funnel 206. Opening 218 is sized and shaped to receive the distal sheath 30 of delivery device 10 therein. The cross-section of tubular extension 216 is preferably substantially circular, but may be oblong, oval, elliptical, or polygonal.

Figure 6A:
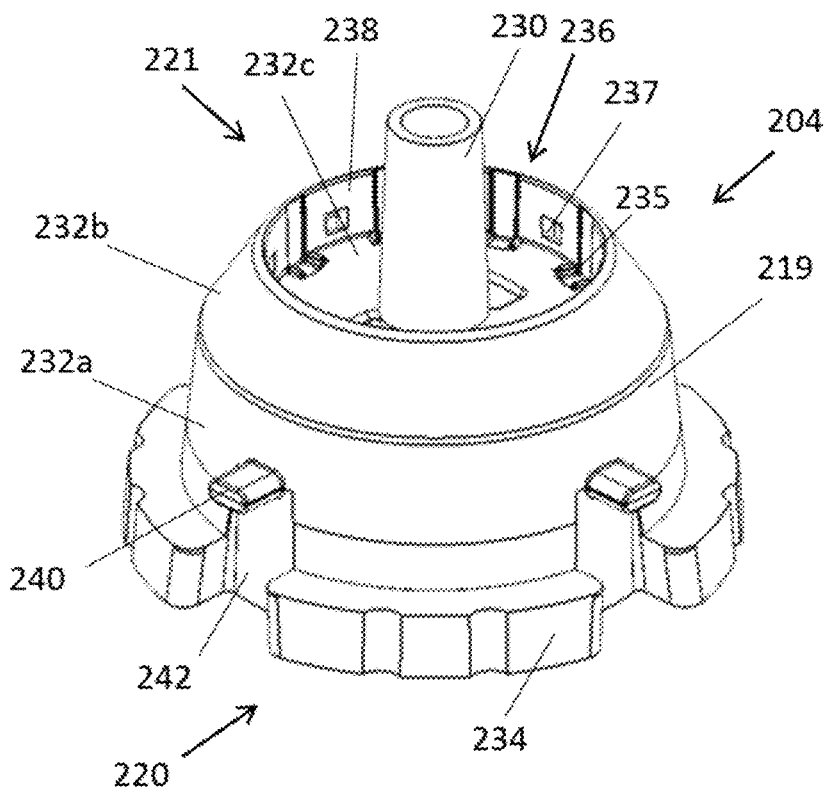
FIG. 6A is a top perspective view of a support member in accordance with an embodiment of the disclosure.
Figure 6B:
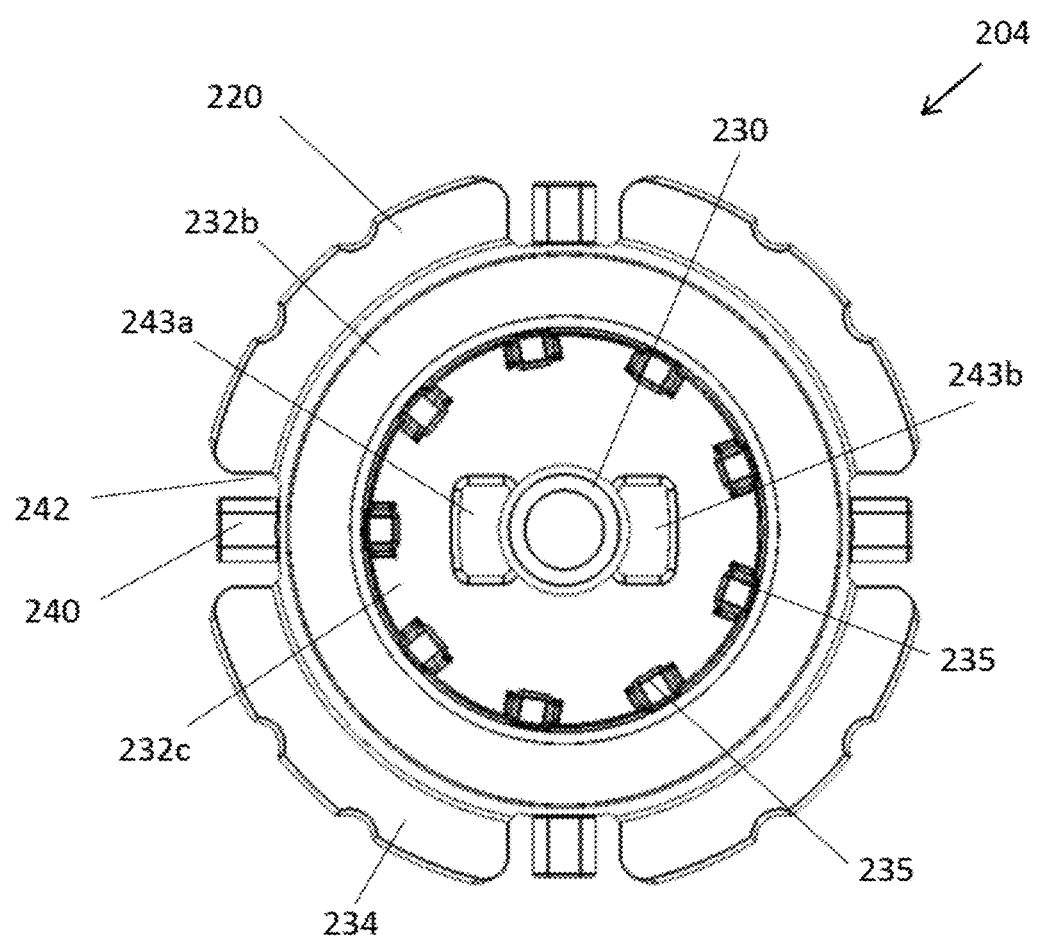
FIG. 6B is a top plan view of the support member of FIG. 6A.
Figure 6C:
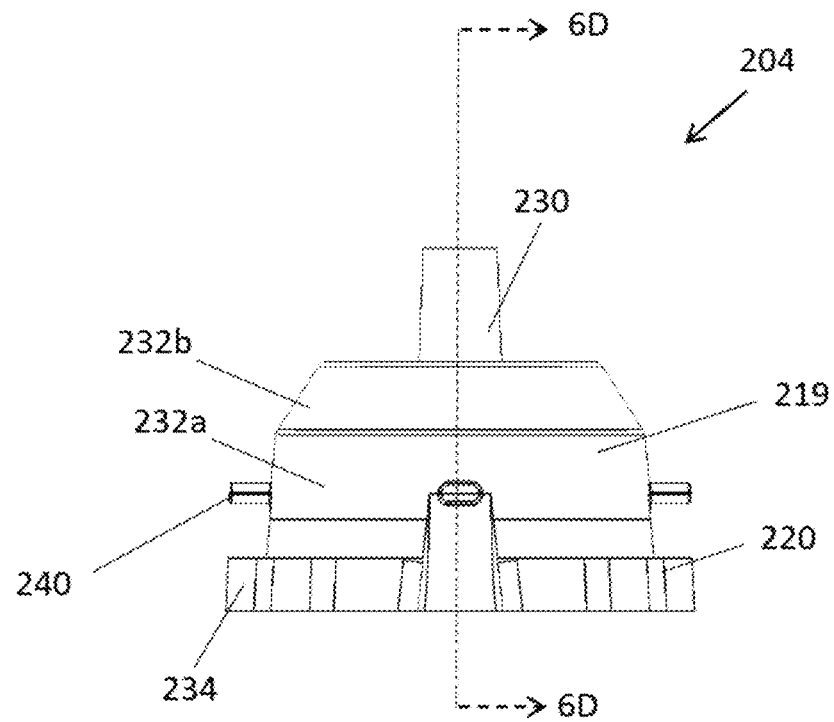
FIG. 6C is a side view of the support member of FIG. 6A.
Figure 6D:
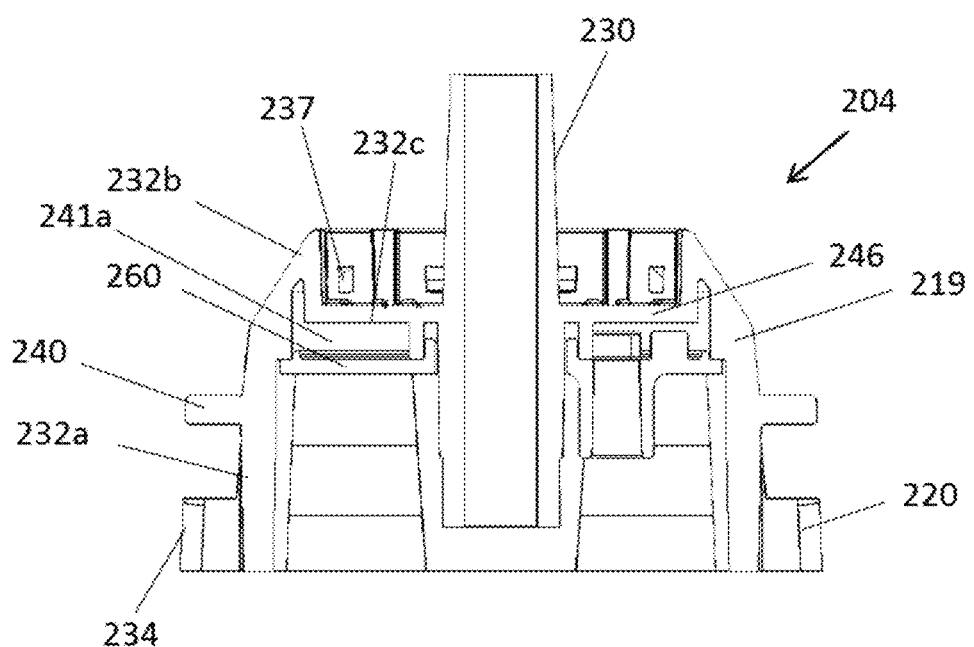
FIG. 6D is a cross-sectional view of the support member of FIG. 6A, taken along section line 6D-6D of FIG. 6C.
Figure 6E:
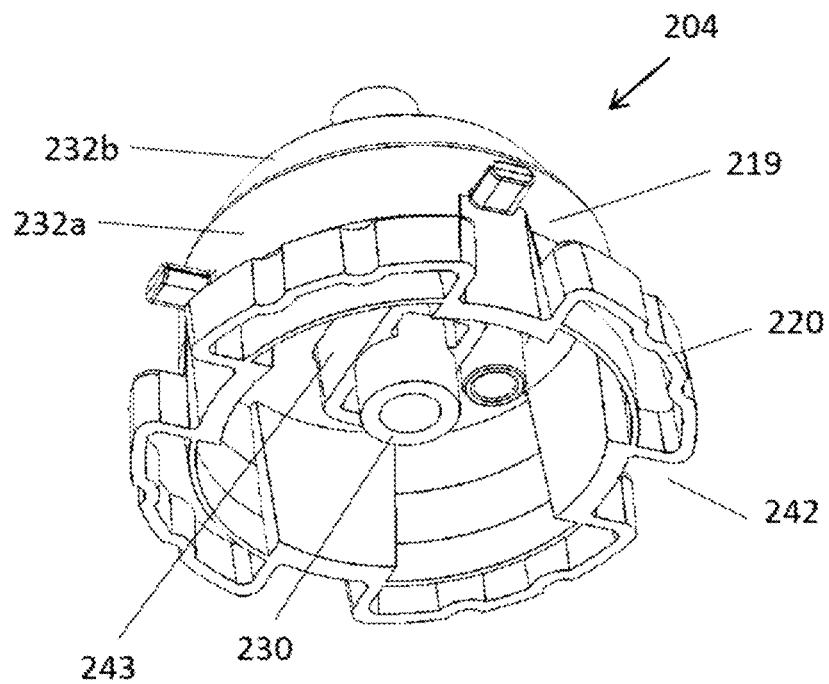
FIG. 6E is a bottom perspective view of the support member of FIG. 6A.
Figure 6F:
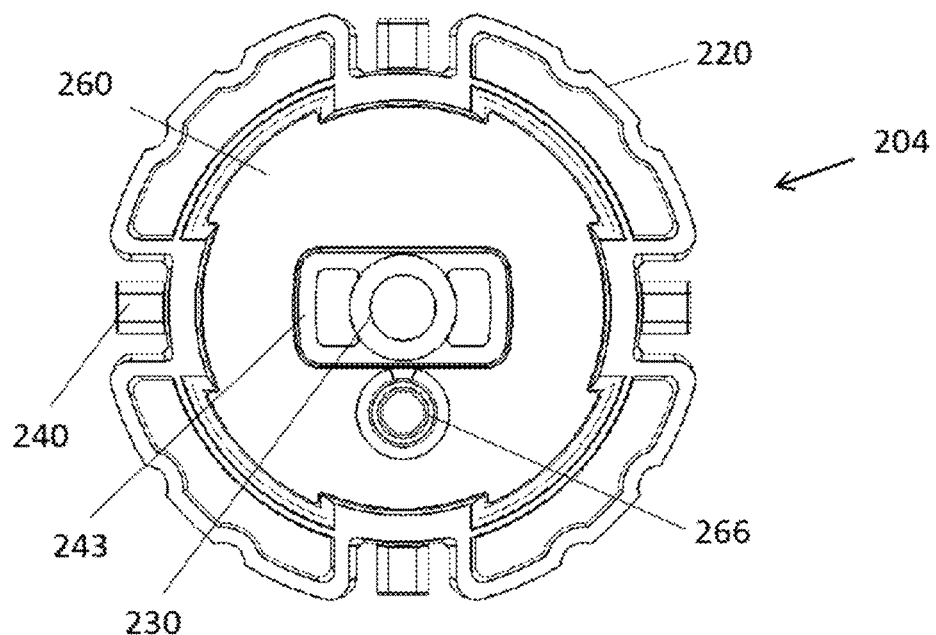
FIG. 6F is a bottom plan view of the support member of FIG. 6A.
Figure 6G:
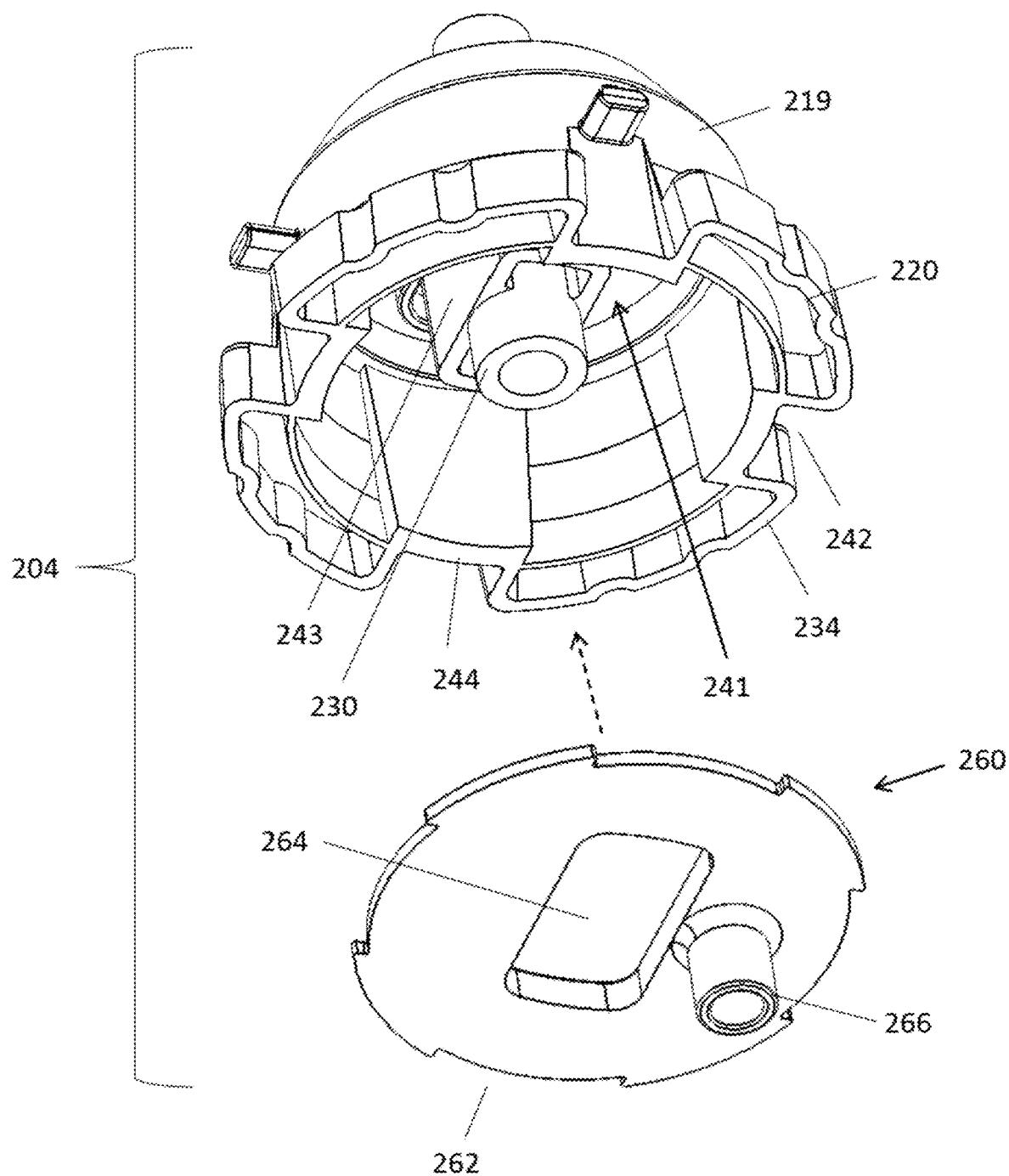
FIG. 6G is an exploded bottom perspective view of a body and a backing plate of the support member of FIG. 6A.
Figure 6H:
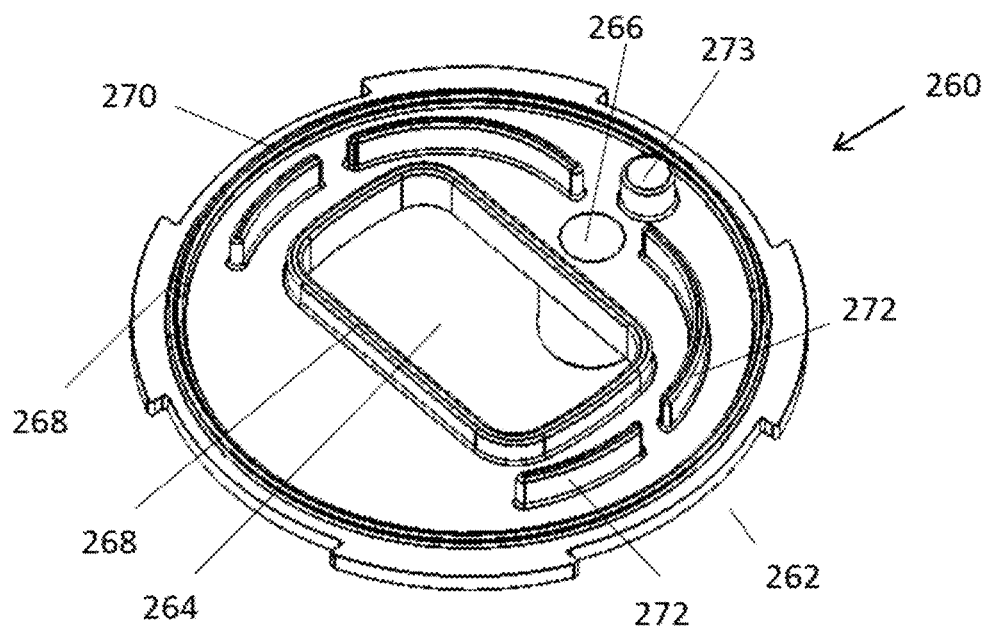
FIG. 6H is a top perspective view of the backing plate of FIG. 6G.

With reference to FIGS. 6A-I, support member 204 is preferably made in whole or in part of a substantially rigid material. Because support member 204 may facilitate a flushing procedure, a void in the support member may be required to provide a desired path for fluid flow. If support member 204 is formed from a process such as injection molding, it may be formed as two separate parts that are joined together to create the void, although it may be possible to form the support member as a single integral body, for example by additive manufacturing or 3D printing. Support member 204 generally includes a body 219 and a backing plate 260 (backing plate 260 is best illustrated in FIGS. 6G-H). Body 219 may have a base 220 and a top end 221, and may include a substantially cylindrical main wall 232a extending from base 220 toward top end 221. Main wall 232a may transition into a top wall 232b, the top wall having an outer surface with a frusto-conical shape that tapers radially inwardly from the main wall toward top end 221. It should be understood that the outer surfaces of main wall 232a and top wall 232b may be complementary to the inner surfaces of rim 214 and funnel 206 of compression member 202, respectively, such that, when the compression member is coupled to support member 204 as described in greater detail below, the assembly may form a snug or even fluid-tight connection between the complementary surfaces.

A recess 236 extends downwardly from the top end 221 of body 219 and includes a bottom member 246 defining a substantially flat seating surface 232c at a spaced distance from the top end. Recess 236 also includes an inner wall 238 circumscribing seating surface 232c. Inner wall 238 may be substantially a surface of revolution about the longitudinal axis of support member 204, while seating surface 232c may be substantially orthogonal to the longitudinal axis. Recess 236 may have a diameter and a depth defined by seating surface 232c sufficient to receive at least a portion of the annulus section 106 of valve 100 in an expanded condition.

Body 219 may be substantially hollow so as to define a void space 241 extending inwardly from base 220 toward top end 221. This void space 241, as best seen in FIG. 6D, may provide a pathway for a fluid injected through inlet port 266 of backing plate 260 to exit outlet ports 237 formed within the inner wall 238 of recess 236, as described in greater detail below.

Seating surface 232c may include features to help secure valve 100 to support member 204, and in particular to position the valve in a desired rotational orientation in the support member. A plurality of recesses or indentations 235 may be equally spaced along the outer circumference of seating surface 232c. Preferably, the number of indentations 235 is the same as the number of horseshoes in stent 102. In the illustrated embodiment, valve 100 includes nine horseshoes and seating surface 232c includes nine indentations 235, with the spacing between adjacent indentations being substantially equal to the spacing between adjacent horseshoes when the valve is in the expanded condition. The inner wall 238 or recess 236 may also include a plurality of outlet ports 237 in fluid communication with the void space 241 in body 219. Preferably, outlet ports 237 are spaced evenly along the perimeter of the inner wall 238, so that each outlet port is positioned between two adjacent indentations 235. With this configuration, when the horseshoes of stent 102 are seated within the indentations 235 of seating surface 232c, the portions of second cuff 115 extending between two adjacent points of attachment 116 are aligned with a corresponding outlet port 237.

Body 219 may also include a tube 230 extending concentrically with the longitudinal axis of support member 204, the tube having a top end extending beyond the top end 221 of the body and a bottom end positioned between seating surface 232c and the bottom of base 220. As best seen in FIG. 6D, tube 230 may have a substantially cylindrical inner surface defining a bore or passageway, and an outer surface that tapers from a relatively large diameter near seating surface 232c to a smaller diameter at the top of the tube. The interior bore of tube 230 is sized and shaped to receive at least a portion of the tip 32 of delivery device 10 therein. The outer surface of the portion of tube 230 extending below seating surface 232c toward base 220 may be substantially cylindrical and may be received within a supporting structure 243 having a rectangular shape with rounded corners. Supporting structure 243, best illustrated in FIGS. 6G and 6I, may, at least in part, define two apertures 243a, 243b (see FIG. 6B) extending though seating surface 232c on opposite sides of tube 230. Depending on the size of the particular valve supported by support member 204, the valve may be supported directly on seating surface 232c, or by a separate base insert (not shown) coupled to the seating surface. For example, the base insert may include a substantially flat top plate with a central aperture for receiving the top of tube 230 therethrough. Two clips or prongs extending from the bottom surface of the top plate are adapted to extend through apertures 243a, 243b. The clips may be biased such that, after passing through apertures 243a, 243b, they spring outwardly to clip onto a bottom edge of support structure 243. The base insert may provide an alternative seating surface that may include features similar to those of seating surface 232c, such as indentations similar to indentations 235 described above, so that a valve may sit on a surface of the base insert that is higher than seating surface 232c. Such a configuration may allow, for example, for a single size base member 204 to be used with a variety of different sized valves, with corresponding base inserts providing for different seating heights depending on the size of the valve and the desired positioning relative to components of loading assembly 200.

The outer surface of main wall 232a may not extend entirely continuously around the body, but rather may be interrupted by a plurality of inward indentations 242. Although FIG. 6A depicts a support member 204 having four indentations 242 evenly spaced around the periphery of body 219, it is contemplated that the support member may be provided with more or less than four such indentations. Indentations 242 may facilitate the grasping of support member 204. At the top of each indentation 242, a pin 240 may protrude radially outward from main wall 232a. Pins 240 are preferably sized and shaped to be received in the slots 228 of compression member 202 to join the compression member and supporting member 204 together. When joined together, compression member 202 and support member 204 collectively define a partial loading assembly 201. The bottom of main wall 232a may transition into a plurality of radially projecting supporting plates 234, each supporting plate being separated from an adjacent supporting plate by an indentation 242, and the supporting plates in the aggregate forming base 220. Supporting plates 234 may include texturization such as ridges to assist a user in gripping support member 204.

Figure 6I:
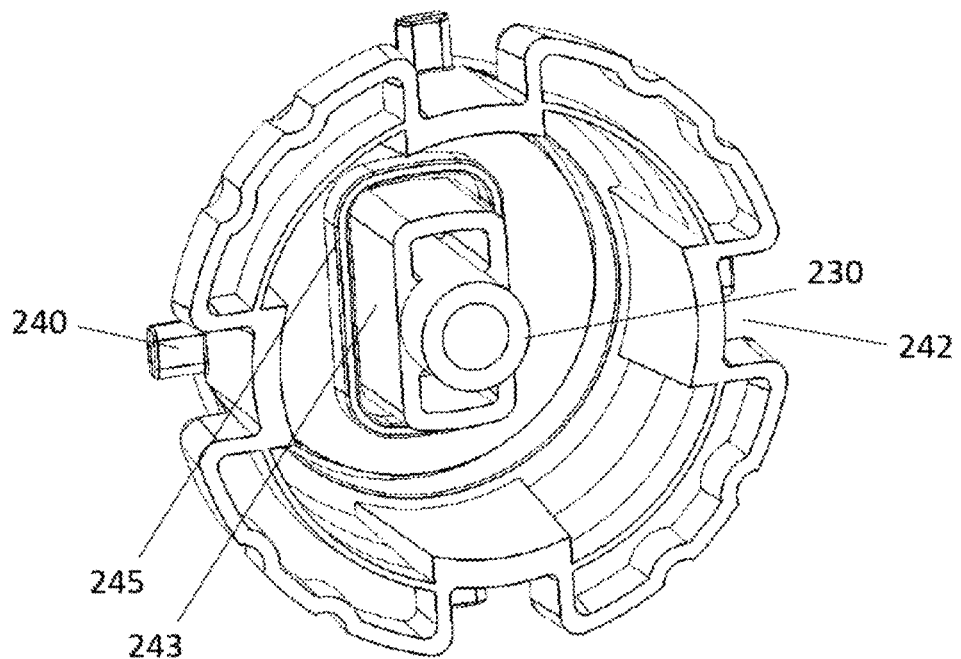
FIG. 6I is a bottom perspective view of the body of FIG. 6G.

As noted above, support member 204 may include body 219 and backing plate 260. Backing plate 260 is best illustrated in FIGS. 6D, 6G, and 6H. FIG. 6I shows a bottom view of body 219 with backing plate 260 removed. Backing plate 260 may be substantially circular with a plurality of indentations 262 in its outer circumference. Preferably, the number of indentations 262 in backing plate 260 is equal to the number of indentations 242 in body 219. As best seen in FIG. 6G, at each location at which there is an indentation 242 in the outer surface of main wall 232a, the indentation forms a corresponding protrusion 244 in the inner surface of the main wall. As a result, the inner diameter of the body is smaller where the protrusions 244 are present. The indentations 262 of backing plate 260 may correspond in size and shape to protrusions 244 such that, when the backing plate is inserted into body 219, the indentations in the backing plate align with the protrusions on the body, rotationally locking the backing plate with respect to the body.

Backing plate 260 may also include an aperture 264 at its center. In the illustrated embodiment, aperture 264 is substantially rectangular with rounded corners, which corresponds to the shape of the supporting structure 243 through which the bottom of tube 230 extends. An inlet port 266 may extend from the bottom surface of backing plate 260 adjacent aperture 264. Inlet port 266 may be shaped to receive a syringe or other fluid injection device such that, when backing plate 260 is assembled to body 219, fluid injected through the inlet port may pass into the portion of void space 241 space between the backing plate and the body, and then exit through outlet ports 237.

The top surface of backing plate 260 is shown in FIG. 6H. Aperture 264 may be surrounded by a first rectangular ridge 268 extending substantially orthogonally from the top surface of backing plate 260. When inserted into body 219, the inner surface of ridge 268 may slide along the outer surface of support structure 243. As shown in FIG. 6I, a second rectangular ridge 245 may extend from the bottom of seating surface 232c, the second rectangular ridge having a shape corresponding to the shape of ridge 268, but with a larger perimeter. When coupling backing plate 260 to body 219, ridge 268 may be sandwiched between ridge 245 and supporting structure 243. Backing plate 260 may also include a circular ridge 270 extending substantially orthogonally from the top of backing plate 260, just radially inward of indentations 262. When backing plate 260 is assembled to body 219, as best illustrated in FIG. 6D, ridge 270 abuts an interior shoulder of body 219. Thus, in the assembled condition, a void space or volume 241a is created between the top surface of backing plate 260, ridges 245 and 270, the bottom of seating surface 232c, and the interior portion of body 219 forming the shoulder contacting the circular ridge, with the void being fluid tight except for inlet port 266 and outlet ports 237. If backing plate 260 and body 219 are formed as separate members coupled together, the backing plate is preferably ultrasonically welded to the body, although other coupling techniques may be used.

As is explained in greater detail below, it is preferable that fluid entering inlet port 266 passes through void space 241a between backing plate 260 and body 219, and exits through all of the outlet ports 237 with a substantially even flow rate and/or pressure. This might be best achieved by positioning inlet port 266 at the longitudinal center of backing plate 260, so that the inlet port is at substantially the radial center of the plurality of outlet ports 237. However, the positioning of tube 230 at the center of body 219 may preclude inlet port 266 from being located at the center of backing plate 260. As such, in the illustrated embodiment, inlet port 266 is positioned a distance away from the center of backing plate 260. Without additional structures, which are described immediately below, fluid passing through inlet port 266 may preferentially flow through the outlet ports 237 positioned nearest the inlet port. Referring to FIG. 6H, a plurality of curved ridges 272 extend from the top of backing plate 260, each curved ridge being positioned between rectangular ridge 268 and circular ridge 270. When backing plate 260 is assembled to body 219, the curved ridges 272 may extend far enough to contact the bottom surface of member 246 or, as in the illustrated embodiment, a clearance may exist between the curved ridges and the bottom surface of member 246. In the illustrated embodiment, there are a total of four curved ridges 272 that extend along a generally oval shape, with each curved ridge being separated from each adjacent curved ridge. Two of the curved ridges 272 are relatively long and positioned near inlet port 266, while the other two of the curved ridges are relatively short and are positioned farther away from the inlet port. Preferably, the curved ridges 272 are symmetrical about a line extending along the diameter of backing plate 260 and through the center of inlet port 266. Curved ridges 272 function to guide a portion of the flow of fluid injected through inlet port 266 along a path around first rectangular ridge 268 and toward the outlet ports 237 farthest away from the inlet port. An additional cylindrical projection 273 may be positioned in radial alignment with inlet port 266 and nearer circular ridge 270 than is the inlet port. Cylindrical projection 273 may serve as an additional structure similar to curved ridges 272 to help guide the flow of fluid injected through inlet port 266 in a desired fashion. As noted above, a complete absence of curved ridges 272 and cylindrical projection 273 may result in fluid preferentially flowing from inlet port 266 to the outlet ports 237 closest to the inlet port. However, with curved ridges 272 and cylindrical projection 273, fluid passing through inlet port 266 may be guided such that the fluid exits all of the outlet ports 237 with substantially the same flow rate and/or pressure. In view of this function, it may be preferable that backing plate 260 is void of ridges similar to curved ridges 272 in areas the greatest distance from inlet port 266, so that fluid is not restricted or inhibited from exiting the outlet ports 237 farthest away from the inlet port.

Figure 7:
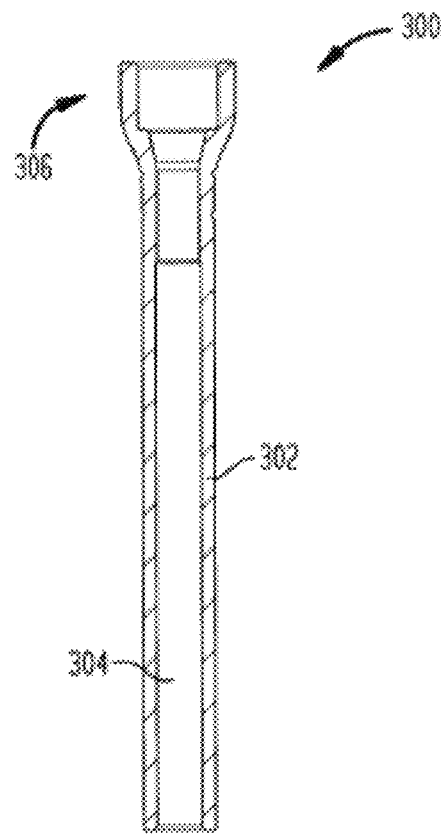
FIG. 7 is a longitudinal cross-sectional view of a constricting member in accordance with an embodiment of the disclosure.
Figure 8:
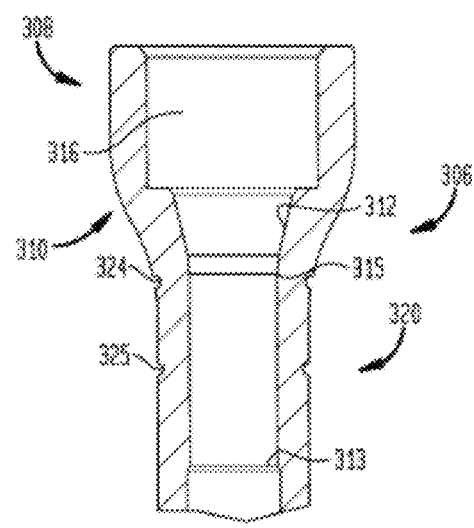
FIG. 8 is an enlarged longitudinal cross-sectional view of an end section of the constricting member of FIG. 7.

FIGS. 7 and 8 illustrate a constricting member 300 designed to minimize the flaring of the distal end 21 of distal sheath 30 during loading of a prosthetic heart valve into the compartment 23 of delivery device 10. Constricting member 300 may be wholly or partly made of a transparent plastic, such as polycarbonate or acrylic, to allow viewing of delivery device 10 during loading and includes a tubular member 302 having a central lumen 304 sized and shaped to slidingly receive at least the distal sheath 30 of delivery device 10.

As seen in FIG. 8, at one end 306, constricting member 300 may have an enlarged head 308 with a counterbore 316 formed therein. Counterbore 316 may have a diameter that is larger than the diameter of lumen 304, and in particular, may be sized and shaped to receive the tubular extension 216 of compression member 202. Preferably, the diameter of counterbore 316 is only slightly larger than the outer diameter of tubular extension 216 so as to create a friction fit therebetween.

Between tubular member 302 and enlarged head 308, constricting member 300 may have a tapered portion 310. In particular, tapered portion 310 may have an inner surface 312 that tapers from a larger diameter at its end adjacent counterbore 316 to a smaller diameter at its other end to help compress valve 100 further during loading into delivery device 10.

Constricting member 300 may further include a transition portion 320 disposed between tapered portion 310 and tubular member 302. Transition portion 320 may have a substantially constant inner diameter sized and shaped to receive at least the distal sheath 30 of delivery device 10. The inner diameter of the transition portion 320 may be slightly smaller than the diameter of lumen 304 and slightly larger than the outer diameter of distal sheath 30 in order to substantially prevent or minimize the flaring of the distal end 21 of the distal sheath while the valve 100 is loaded in the delivery device 10. The larger diameter of lumen 304 allows a user to easily slide constricting member 300 over the distal sheath 30 of delivery device 10. In a variant hereof, the transition portion 320 may have an inner diameter which tapers downwardly from a slightly larger diameter at an end 313 thereof to a slightly smaller diameter at an end 315 thereof to accommodate small variations in the outer diameter of distal sheath 30.

An annular groove or other indicator line 324 may extend partly or entirely around the outer periphery of tubular member 302 at the junction between tapered portion 310 and transition portion 320. Another annular groove or indicator line 325 may extend partly or entirely around the outer periphery of tubular member 302 at a spaced distance from the first line 324. Lines 324 and 325 mark the area in which the user should place the distal end 21 of distal sheath 30 during the loading procedure. Using constricting member 300 to help load valve 100 into delivery device 10 reduces the loading forces (i.e., the forces required to load the valve into the delivery device) and reduces flaring of the distal end 21 of distal sheath 30.

Figure 9:
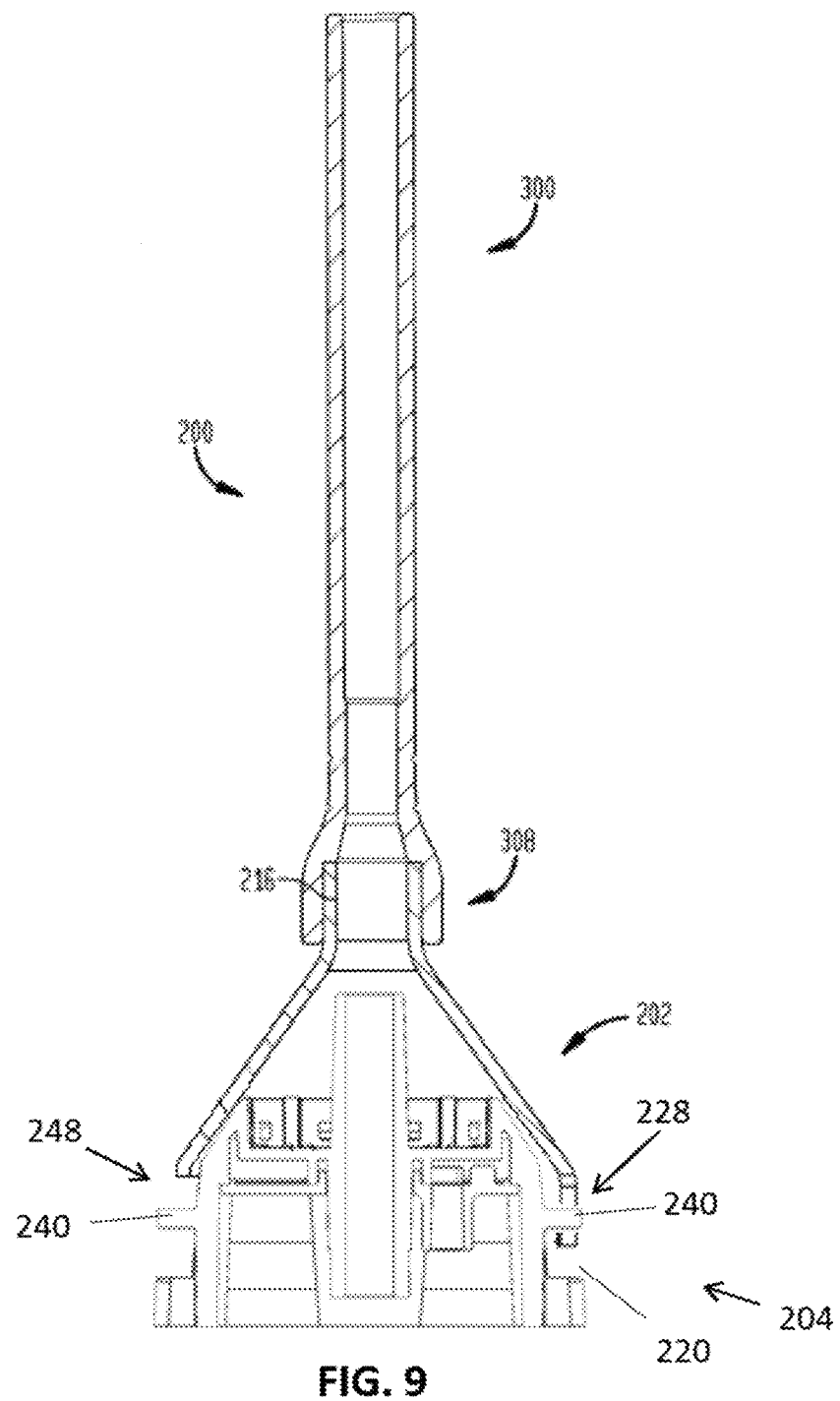
FIG. 9 is a longitudinal cross-sectional view of a loading assembly in accordance with an embodiment of the present disclosure, including the compression member of FIG. 5, the support member of FIG. 6A, and the constricting member of FIG. 7.

FIG. 9 shows an assembled loading assembly 200 including compression member 202, support member 204, and constricting member 300. As seen in FIG. 9, constricting member 300 is connected by its enlarged head 308 to the tubular extension 216 of compression member 202, and the compression member is locked to support member 204. To lock compression member 202 to support member 204, the pins 240 of the support member are inserted into the slots 228 of the compression member, and the compression member is rotated relative to the support member to slide the pins toward the closed ends of the slots. Hence, pins 240 and slots 228 together form a locking mechanism 248. Rather than the engagement of pins 240 in slots 228, it is contemplated that any other known locking mechanisms may be employed to securely lock compression member 202 to support member 204.

Figure 10:
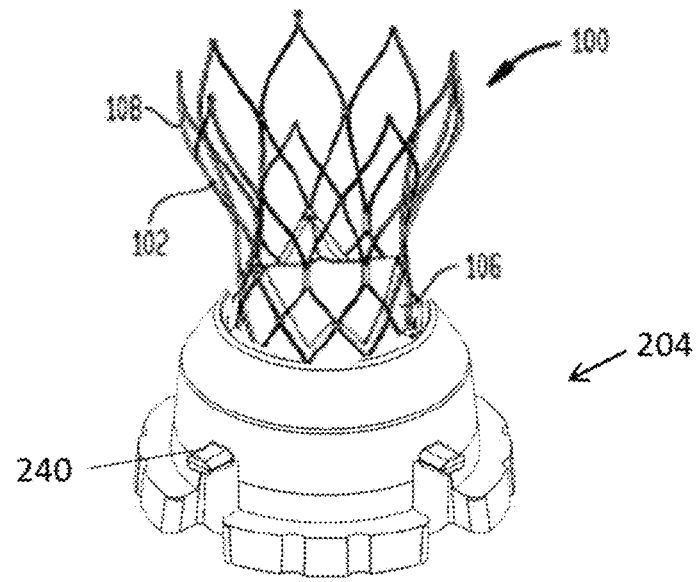
FIGS. 10-19 illustrate the steps of a method for loading a prosthetic heart valve into a delivery device using the loading assembly of FIG. 9.
Figure 11:
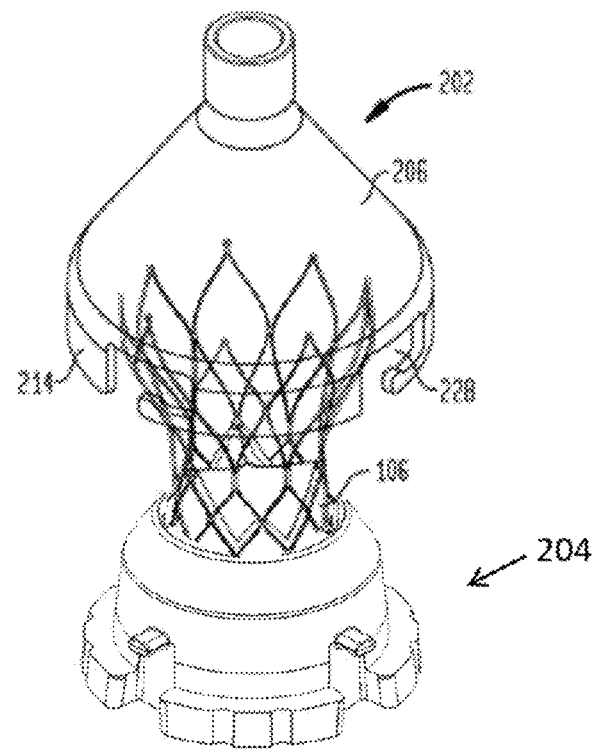
Figure 12:
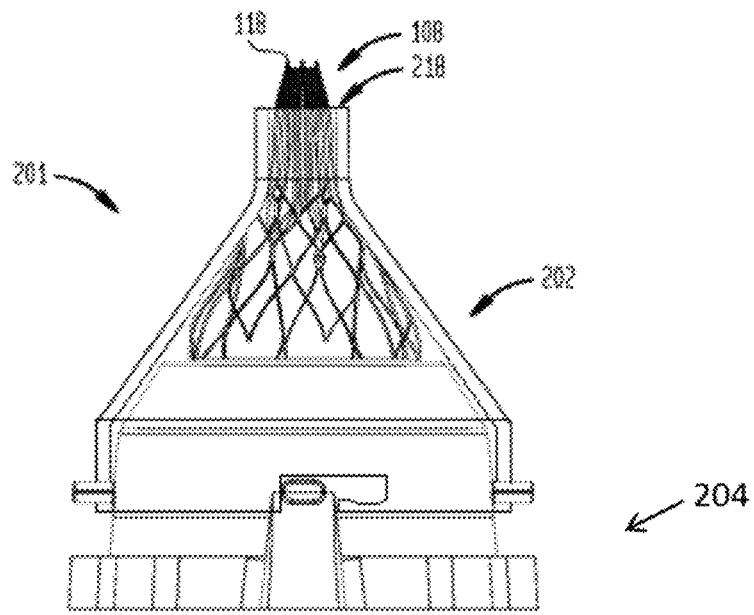
Figure 13:
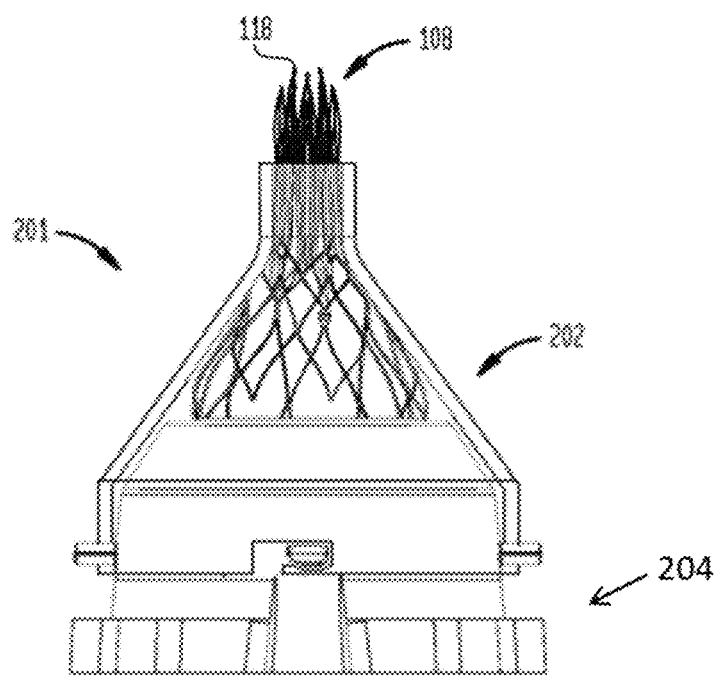

As seen in FIGS. 10-19, loading assembly 200 may be used to load collapsible prosthetic heart valve 100 into delivery device 10. As shown in FIG. 10, with support member 204 on a flat surface, the horseshoes at the inflow end of stent 102 may be placed within indentations 235 on seating surface 232c so that the centers of the free edges 117 of second cuff 115 rotationally align with respective outlet ports 237. It should be understood that it may be preferable for the valve 100 to be positioned such that portions of second cuff 115 in axial alignment with the center of corresponding free edges 117, but positioned an axial distance from the free edges in the direction toward the inflow edge, are in rotational alignment with outlet ports 237. Compression member 202 may then be placed over the aortic section 108 of stent 102 so that the aortic section of the stent is positioned within funnel 206, as depicted in FIG. 11. As shown in FIG. 12, the compression member 202 and the support member 204 may then be pushed together, the tapered walls of the funnel 206 gradually compressing the valve 100 until a portion of the aortic section 108 of the stent 102 is forced into and through the opening 218 of the compression member. When a portion of the aortic section 108 of stent 102 passes through the opening 218 of compression member 202, the retainers 118 of the stent will protrude through opening 218 and will be positioned closely adjacent to one another. At this point, the pins 240 of support member 204 will be positioned within the slots 228 of compression member 202, and the members may be locked together by rotating the support member relative to the compression member, as shown in FIG. 13, such that the pins 240 of the support member slide toward the closed ends of the slots 228 of the compression member.

Figure 14A:
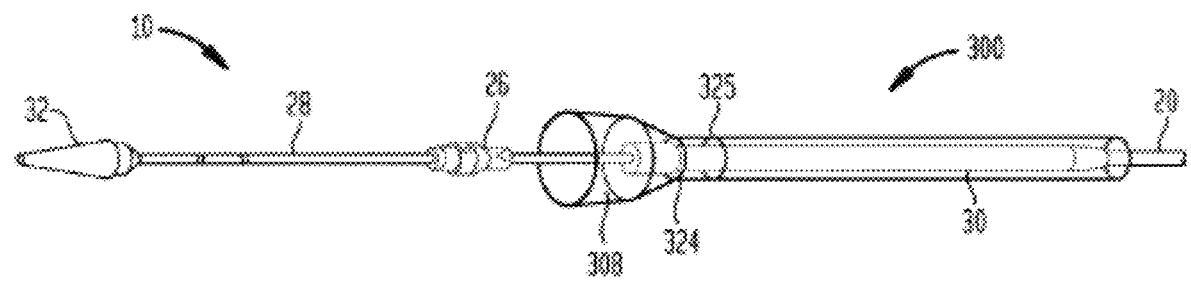

As seen in FIG. 14A, with distal sheath 30 in a proximal or open position, constricting member 300 may be placed over delivery device 10 with enlarged head 30 positioned closer to the tip 32 than to the hub or handle of the delivery device, and with the distal end 21 of distal sheath 30 longitudinally positioned between indicator lines 324 and 325 of the constricting member. It will be appreciated that constricting member 300 also may be placed over the delivery device 10 with distal sheath 30 in the distalmost or closed position, and that the distal sheath subsequently may be moved to the proximal or open position.

Figure 14B:
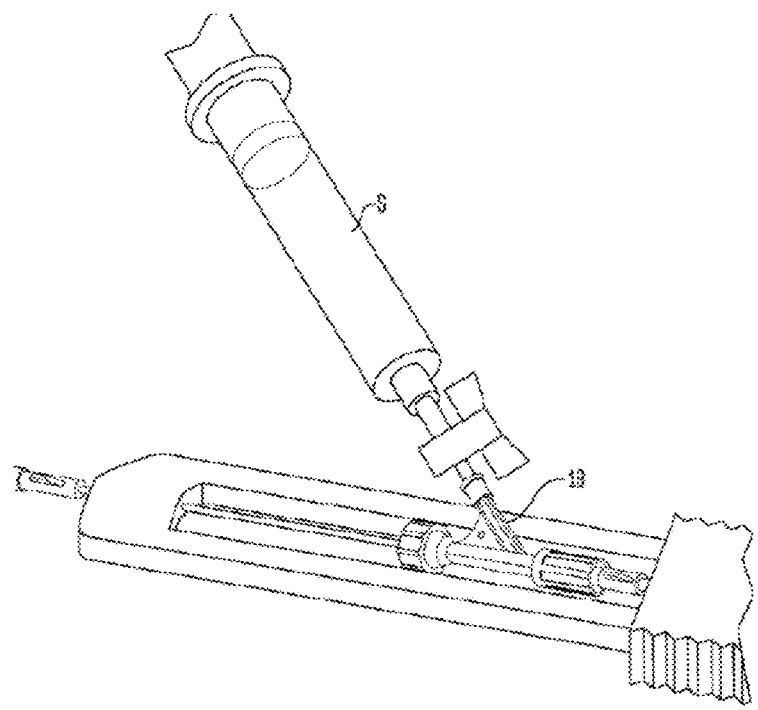

Before loading valve 100 into delivery device 10, it is preferable to subject the delivery device to a flushing or deairing process. In that regard, with constricting member 300 assembled over distal sheath 30 and the distal sheath in an open position, a syringe S may be connected to the Y-connector 18 of delivery device 10, as shown in FIG. 14B. The syringe may be used to inject a sterile liquid, such as saline, into the proximal end of the delivery device and out through open compartment 23, thereby flushing the air from the device. During this flushing step, the distal end of the delivery device may be tapped multiple times to facilitate the air removal. After this flushing step, it is preferable that delivery device 10 and constricting member 300 remain positioned upright, such that tip 32 and enlarged opening 308 point in a direction opposite gravity. This positioning may help ensure that fluid within the system from the flushing step remains in the system during loading of valve 100.

Figure 15:
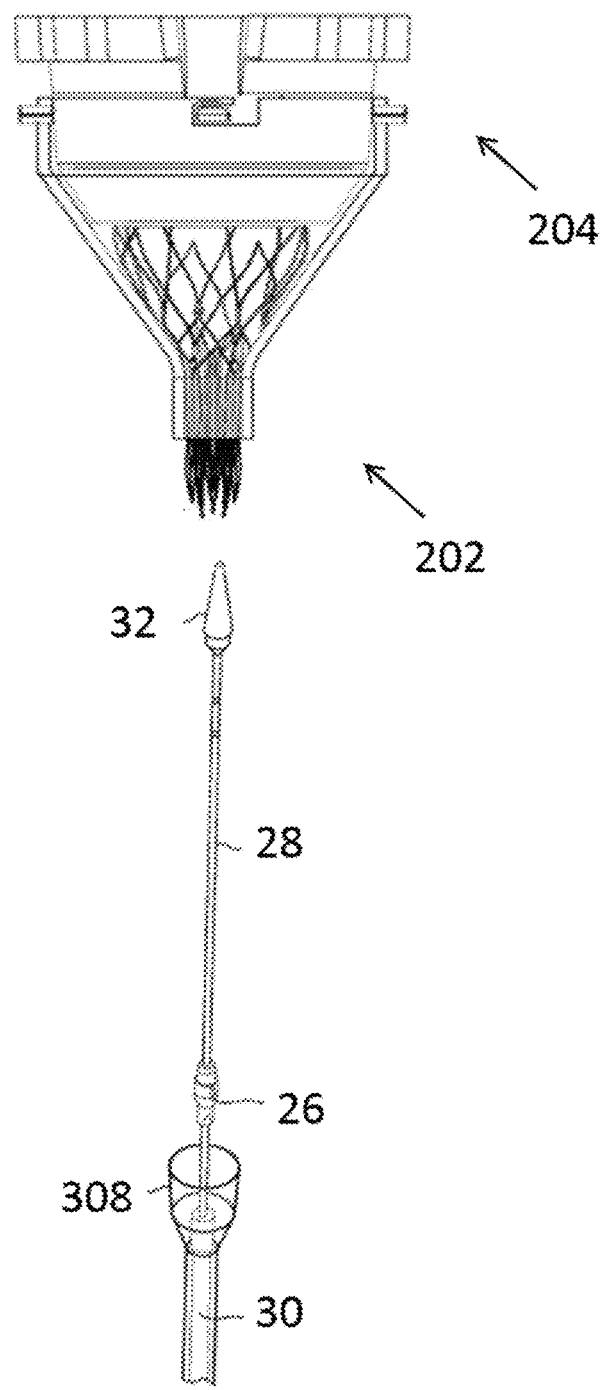
Figure 16:
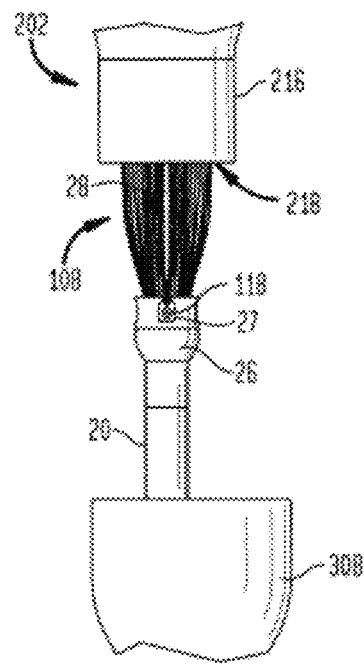
Figure 17:
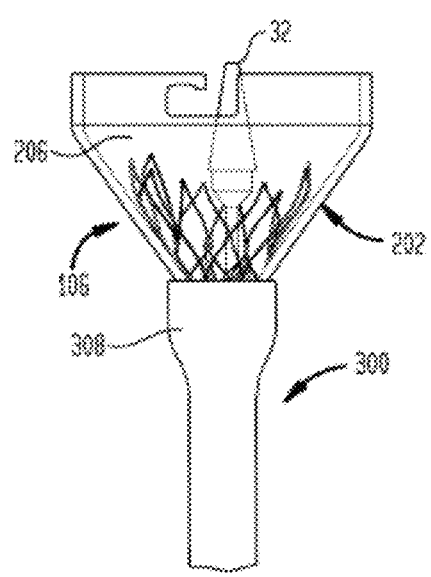

Once flushing of delivery device 10 has been completed, the tip 32 and the support shaft 28 of the delivery device may be inserted into the end of the collapsed valve 100 protruding from the opening 218 of compression member 202. To accomplish this, compression member 202 and support member 204 may be squeezed closer together. (The dimension of slots 228 in the longitudinal direction, i.e., the height of the slots, is greater than the dimension of pins 240 in the longitudinal direction, i.e., the height of the pins. Therefore, even though compression member 202 and support member 204 are assembled together, they still may move further toward one another.) As compression member 202 and support member 204 move closer together, a greater portion of stent 102 is forced out through opening 218, causing retainers 118 to begin to separate from one another, as illustrated in FIG. 13. The tip 32 and the support shaft 28 of delivery device 10 may then be inserted between retainers 118 and into the end of collapsed valve 100, as shown in FIG. 15. Partial loading assembly 201 may be advanced along support shaft 28 until the retainers 118 of stent 102 are positioned over the retaining element 26 of delivery device 10. Partial loading assembly 201 may be twisted as needed to align retainers 118 with the recesses 27 in retaining element 26. Positioning retainers 118 within the recesses 27 of retaining element 26 attaches stent 102 to delivery device 10, as seen in FIG. 16. With stent 102 attached to retaining element 26, constricting member 300 and distal sheath 30 may be slid together toward partial loading assembly 201 (or inner tube 16 may be moved proximally relative to constricting member 300 and distal sheath 30) to about the position shown in FIG. 17, in which the distal sheath covers the retainers 118 of the stent, at the same time maintaining the distal end 21 of the distal sheath between the indicator lines 324 and 325 of the constricting member. The tapered inner surface 312 of enlarged head 308 facilitates the compression of stent 102 as it moves into constricting member 300. When constricting member 300 and partial loading assembly 201 are close together, they may be joined to one another by assembly of the enlarged head 308 of the constricting member to the tubular extension 216 of compression member 202. It should be understood that, although compression member 202 in FIG. 17 is shown as unattached to support member 204, the support member preferably remains attached to the compression member at this stage of the loading procedure in order to facilitate an additional flushing step.

In order to flush or deair the valve 100, a sterile liquid, such as saline, may be injected through the inlet port 266 of the backing plate 260 of support member 204, for example using a syringe. The relative rotational positioning between outlet ports 237 and the free edges 116 of second cuff 115 allows for fluid injected through inlet port 266 of backing plate 260 to travel through the void space 241a in body 219, and to exit the outlet ports, wherein the fluid contacts the free edges of the second cuff and portions of the second cuff axially aligned with the free edges as part of a deairing or flushing procedure. As the liquid passes through inlet port 266, it preferably interacts with curved ridges 272 and/or cylindrical projection 273 such that the liquid flows substantially equally through each of the outlet ports 237. During this portion of the deairing process, it should be understood that valve 100 is inverted compared to the view shown in FIG. 4, such that the free edges 117 of second cuff 115 are positioned closer to the ground (or farther in the direction in which gravity acts) compared to the inflow ends of first cuff 114 and the second cuff. As the liquid is injected through inlet port 266, and compression member 202 begins to fill with liquid, it may be important to ensure that large air bubbles do not get trapped between first cuff 114 and second cuff 115. Any air bubbles existing between first cuff 114 and second cuff 115 may tend to move in a direction opposite gravity, or in other words the air bubbles may become trapped in the pocket between the first and second cuffs because the inlet ends of the first and second cuffs are coupled together. However, the positioning of outlet ports 237 relative to second cuff 115 may help ensure that the force provided by the liquid exiting the outlet ports pushes any trapped air bubbles downward (in the direction of gravity) such that they may escape beyond the free edge 117 of the second cuff to exit the system. In view of this particular function, it may be preferable for a portion of second cuff 115 near its inflow edge, but in axial alignment with the center of free edge 117, to be aligned with a corresponding outlet port 237 during this portion of the deairing process.

Once compression member 202 is partially or completely filled with liquid, support member 204 may be disassembled from the compression member by first rotating the support member relative to the compression member, such that the pins 240 of the support member slide toward the open ends of the slots 228 of the compression member. This action unlocks the members from one another. Support member 204 may then be moved away from compression member 202 to disassemble partial loading assembly 201. With the first open end 208 of funnel 206 facing up, additional sterile liquid may be dispensed into the compression member 202 through the first open end if desired.

Figure 18:
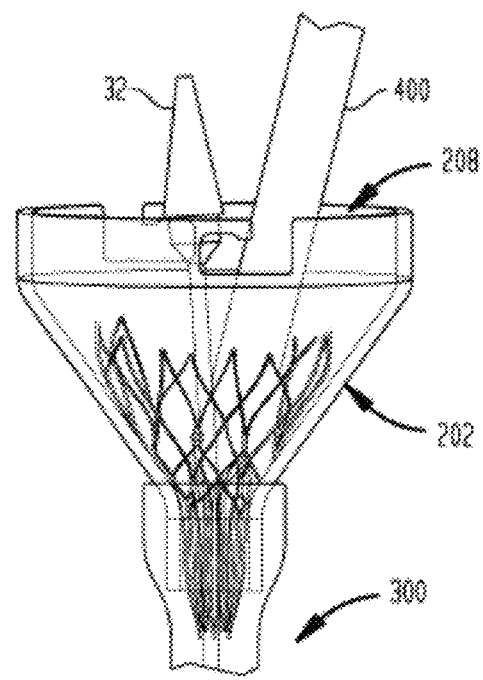
Figure 19:
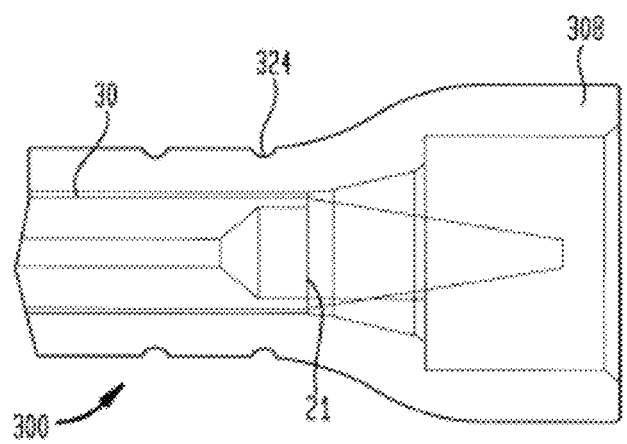

Any additional air bubbles in the sterile liquid within funnel 206 may then be removed in a further step. For example, air bubbles formed in the sterile liquid near the space between the leaflets 112 and the first cuff 114 of valve 100 may be removed by using a tube or rod 400 or any other suitable atraumatic probe. The tube 400 is commonly known in the art as a "leaflet tester" and may be formed of a substantially soft material, such as a soft polymer. In order to remove the air bubbles from the sterile liquid, tube 400 may be placed into the sterile liquid contained in the funnel 206 of compression member 202 and used to probe areas of potential air entrapment, including gently agitating the liquid, as shown in FIG. 18. A syringe may be used to remove the air bubbles from the space near the retaining element 26 of delivery device 10. To do so, the syringe may be inserted into the space near retaining element 26, and the sterile liquid near the retaining element may be gently agitated with the syringe. After the air bubbles have been removed, valve 100 may be pulled into distal sheath 30 until the valve is completely covered, as seen FIG. 19. Constricting member 300 and compression member 202 may then be removed from delivery device 10. The inner tube 16 of delivery device 10 may then be flushed with any suitable sterile liquid using, for example, a syringe. To flush inner tube 16, a syringe may be connected to the hemostatic valve near the hub 14 of delivery device 10, and then sterile liquid may be injected into the inner tube using the syringe.

Figure 20:
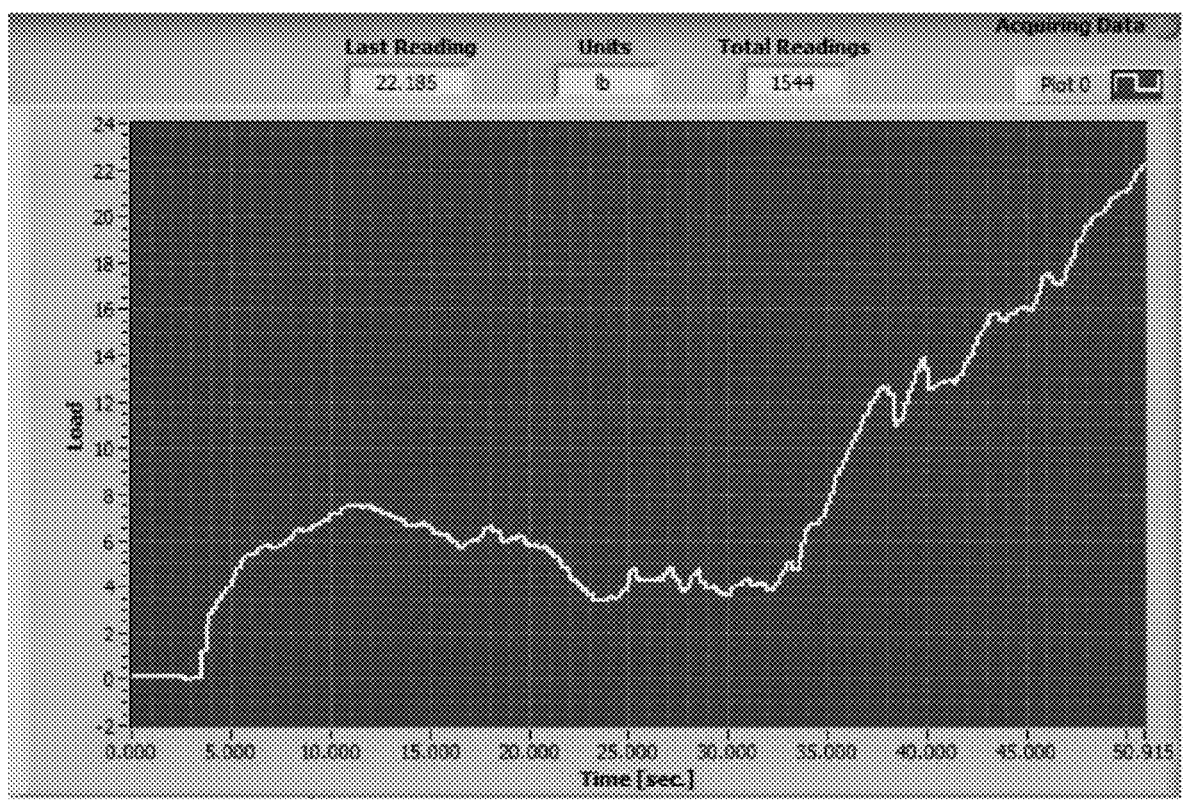
FIG. 20 is a graph showing the increase in loading forces experienced when the second cuff of the valve of FIG. 4 becomes caught on the distal end of the distal sheath of the delivery device of FIG. 1 during valve loading.

One particular issue that may occur during the final stages of loading valve 100 into delivery device 10 is that one or more of the free edges 117 of second cuff 115 may catch on the distal end 21 of distal sheath 30. If one or more of the free edges 117 of second cuff 115 do catch or otherwise snag the distal end 21 of distal sheath 30, the force required to complete the loading procedure may significantly increase. For example, as shown on the graph of FIG. 20, during a typical loading of valve 100 onto delivery device 10, the loading forces are expected to increase to some degree near the completion of loading, represented on the graph as from about 32 seconds to about 41 seconds after beginning to pull the valve into the distal sheath, where the loading force increases from about 4 pounds to about 13 pounds. However, FIG. 20 illustrates that, if one or more of the free edges 117 of second cuff 115 catch on the distal end 21 of distal sheath 30, the loading forces can further significantly increase, shown on the graph as from about 41 seconds to about 51 seconds, where the loading force increases from about 13 pounds to about 22 pounds. This additional increase in loading force may be problematic. First, the increased force in general may cause damage to internal components of delivery device 10, which may cause performance problems during the surgical procedure. Second, if the increased loading force is due to one or more free edges 117 of second cuff 115 catching on the distal end 21 of distal sheath 30, the distal end of the distal sheath may permanently deform, for example a divot or other imperfection may be formed in the distal end of the distal sheath. Such imperfections could create potential problems during the surgical procedure, for example a divot in the distal end 21 of distal sheath 30 may create a sharp edge that may cause trauma to the blood vessels or other patient anatomy as delivery device 10 is advanced through the vasculature. In addition to damage to delivery device 10, this scenario could also lead to damage to valve 100, including damage to sutures (such as fraying or rupturing) or damage to one or both cuffs 114, 115 (for example tearing).

The procedures described above for deairing valve 100 by injecting liquid through inlet port 266 of support member 204 and out of outlet ports 237 may significantly decrease the likelihood of any of the free edges 117 of second cuff 115 catching on the distal end 21 of distal sheath 30. Because the outlet ports 237 are generally aligned with the centers of the free edges 117 of second cuff 115 (or portions of the second cuff in axial alignment with the centers of the free edges), the force of the liquid on the second cuff tends to push the free edges radially inward toward first cuff 114. In other words, after the deairing process using support member 204, the free edges 117 of second cuff 115 are generally pressed against first cuff 114, such that there is little material of the free edge available to catch or snag on the distal end 21 of distal sheath 30 as the second cuff passes over the distal sheath.

It should be understood that support member 204 may be used to flush or deair valve 100 at a different stage in the sequence of loading. For example, liquid may be injected through inlet port 266 prior to inverting valve 100 and partial loading assembly 201 for connection to delivery device 10. Partial loading assembly 201 may then be inverted and coupled to delivery device 10, with the loading procedure otherwise being similar. However, in practice, it is preferable to perform the deairing of valve 100 using support member after inverting and connecting partial loading assembly 201 to delivery device 10 and constricting member 300.

Additional benefits of certain components described herein, as well as additional variants of the support member, compression member, and constricting member, are described in greater detail in U.S. Pat. No. 9,021,674, the disclosure of which is hereby incorporated by reference herein.

According to a first aspect of the disclosure, an assembly for loading a self-expanding prosthetic heart valve into a delivery device, comprises:

a support member including a generally hollow body and a backing plate, the body having a longitudinal axis, a base end, a second end, and a recess extending along the longitudinal axis from the second end toward the base end, the recess having a bottom member defining a seating surface adapted to support the prosthetic heart valve, the backing plate being fixed to the body so as to define a void space between the backing plate and the body, wherein the backing plate includes an inlet port and the recess includes a plurality of outlet ports, the inlet port and the outlet ports being in fluid communication with the void space; and/or the backing plate is integral with the body; and/or the backing plate is non-integral with the body; and/or the plurality of outlet ports are equally spaced along a perimeter of the recess; and/or the inlet port is offset from the longitudinal axis of the body; and/or the backing plate includes a first surface facing the void space and a second surface opposite the first surface; and/or the backing plate includes a plurality of ridges extending substantially orthogonally from the first surface of the backing plate; and/or the bottom member has a second surface opposite the seating surface and the plurality of ridges extend toward the bottom member without contacting the second surface of the bottom member; and/or a perimeter of the seating surface includes a plurality of indentations; and/or the plurality of indentations are equally spaced along circumference perimeter of the seating surface; and/or each of the plurality of indentations is positioned between an adjacent pair of the outlet ports; and/or a tube extending from the seating surface, a longitudinal axis of the tube being coaxial with the longitudinal axis of the body; and/or the tube defines a cylindrical interior bore; and/or the prosthetic heart valve positioned in the recess and supported by the seating surface; and/or the prosthetic heart valve includes a stent, a valve assembly supported by the stent, a first cuff coupled to the stent, and a second cuff coupled to at least one of the stent and the first cuff, the second cuff being positioned on an ablumenal surface of the stent, the prosthetic heart valve having an expanded condition and a collapsed condition; and/or the stent is formed by a plurality of struts, an inflow end of the stent including a plurality of strut intersections; and/or a perimeter of the seating surface includes a plurality of indentations, a spacing between adjacent ones of the indentations being equal to a spacing between adjacent ones of the strut intersections when the prosthetic heart valve is in the expanded condition; and/or the second cuff includes an outflow edge having a plurality of connection points to the prosthetic heart valve and a plurality of free edges extending between adjacent connection points; and/or each of the free edges forms an edge of a pocket between the first cuff and the second cuff; and/or when the prosthetic heart valve is in the expanded condition and each of the strut intersections is received within a corresponding one of the indentations, each of the outlet ports is rotationally aligned with a corresponding one of the pockets.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. An assembly for loading a self-expanding prosthetic heart valve into a delivery device, comprising:
    a support member including a generally hollow body and a backing plate, the body having a longitudinal axis, a base end, a second end, and a recess extending along the longitudinal axis from the second end toward the base end, the recess having a bottom member defining a seating surface adapted to support the prosthetic heart valve, the backing plate being fixed to the body so as to define a void space between the backing plate and the body,
    wherein the backing plate includes an inlet port and the recess includes a plurality of outlet ports, the inlet port and the outlet ports being in fluid communication with the void space.

2. The assembly of claim 1, wherein the backing plate is integral with the body.

3. The assembly of claim 1, wherein the backing plate is non-integral with the body.

4. The assembly of claim 1, wherein the plurality of outlet ports are equally spaced along a perimeter of the recess.

5. The assembly of claim 1, wherein the inlet port is offset from the longitudinal axis of the body.

6. The assembly of claim 5, wherein the backing plate includes a first surface facing the void space and a second surface opposite the first surface.

7. The assembly of claim 6, wherein the backing plate includes a plurality of ridges extending substantially orthogonally from the first surface of the backing plate.

8. The assembly of claim 7, wherein the bottom member has a second surface opposite the seating surface and the plurality of ridges extend toward the bottom member without contacting the second surface of the bottom member.

9. The assembly of claim 1, wherein a perimeter of the seating surface includes a plurality of indentations.

10. The assembly of claim 9, wherein the plurality of indentations are equally spaced along circumference perimeter of the seating surface.

11. The assembly of claim 9, wherein each of the plurality of indentations is positioned between an adjacent pair of the outlet ports.

12. The assembly of claim 1, further comprising a tube extending from the seating surface, a longitudinal axis of the tube being coaxial with the longitudinal axis of the body.

13. The assembly of claim 12, wherein the tube defines a cylindrical interior bore.

14. The assembly of claim 1, further comprising the prosthetic heart valve positioned in the recess and supported by the seating surface.

15. The assembly of claim 14, wherein the prosthetic heart valve includes a stent, a valve assembly supported by the stent, a first cuff coupled to the stent, and a second cuff coupled to at least one of the stent and the first cuff, the second cuff being positioned on an ablumenal surface of the stent, the prosthetic heart valve having an expanded condition and a collapsed condition.

16. The assembly of claim 15, wherein the stent is formed by a plurality of struts, an inflow end of the stent including a plurality of strut intersections.

17. The assembly of claim 16, wherein a perimeter of the seating surface includes a plurality of indentations, a spacing between adjacent ones of the indentations being equal to a spacing between adjacent ones of the strut intersections when the prosthetic heart valve is in the expanded condition.

18. The assembly of claim 17, wherein the second cuff includes an outflow edge having a plurality of connection points to the prosthetic heart valve and a plurality of free edges extending between adjacent connection points.

19. The assembly of claim 18, wherein each of the free edges forms an edge of a pocket between the first cuff and the second cuff.

20. The assembly of claim 19, wherein when the prosthetic heart valve is in the expanded condition and each of the strut intersections is received within a corresponding one of the indentations, each of the outlet ports is rotationally aligned with a corresponding one of the pockets.

* * * * *